US009709785B2

(12) United States Patent
Nomura

(10) Patent No.: US 9,709,785 B2
(45) Date of Patent: *Jul. 18, 2017

(54) STRUCTURED ILLUMINATION APPARATUS, STRUCTURED ILLUMINATION MICROSCOPY APPARATUS, AND PROFILE MEASURING APPARATUS

(71) Applicant: NIKON CORPORATION, Tokyo (JP)

(72) Inventor: Tatsushi Nomura, Sagamihara (JP)

(73) Assignee: NIKON CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/861,091

(22) Filed: Apr. 11, 2013

(65) Prior Publication Data

US 2013/0229665 A1    Sep. 5, 2013

Related U.S. Application Data

(63) Continuation of application No. PCT/JP2011/005682, filed on Oct. 11, 2011.

(30) Foreign Application Priority Data

Oct. 14, 2010   (JP) ................................. 2010-231458
Apr. 11, 2011   (JP) ................................. 2011-087068

(51) Int. Cl.
*G01B 9/02*   (2006.01)
*G02B 21/06*   (2006.01)
(Continued)

(52) U.S. Cl.
CPC .............. *G02B 21/06* (2013.01); *G01B 11/24* (2013.01); *G02B 21/16* (2013.01); *G01N 21/6458* (2013.01); *G02B 2207/113* (2013.01)

(58) Field of Classification Search
CPC ........ G02B 21/06; G02B 21/16; G02B 11/24; G02B 21/0056; G02B 2207/113; G01B 11/24; G01N 21/6458
(Continued)

(56) References Cited

U.S. PATENT DOCUMENTS 4,561,727 A  *  12/1985  Heeks et al. ..................... 349/22
5,182,665 A  *  1/1993  O'Callaghan et al. ........ 349/201
(Continued)

FOREIGN PATENT DOCUMENTS

JP    A-11-242189    9/1999
JP    A-11-295607    10/1999
(Continued)

OTHER PUBLICATIONS

Apr. 16, 2013 International Preliminary Report on Patentability issued in Application No. PCT/JP2011/005682 (with translation).
(Continued)

*Primary Examiner* — Michael A Lyons
(74) *Attorney, Agent, or Firm* — Oliff PLC

(57) ABSTRACT

A structured illumination apparatus includes a light modulator being disposed in an exit flux of light from a light source and in which a sonic wave propagation path is arranged in a direction traversing the exit flux of light; a driving unit generating a sonic standing wave in the sonic wave propagation path by giving a driving signal for vibrating a medium of the sonic wave propagation path to the light modulator; and an illuminating optical system making mutually different diffracted components of the exit flux of light passed through the sonic wave propagation path to be interfered with each other, and forming interference fringes of the diffracted components on an observational object.

24 Claims, 10 Drawing Sheets

(51) Int. Cl.
  *G01B 11/24* (2006.01)
  *G02B 21/16* (2006.01)
  *G01N 21/64* (2006.01)

(58) Field of Classification Search
  USPC .................. 356/499, 521, 601, 618; 359/385
  See application file for complete search history.

(56) References Cited

U.S. PATENT DOCUMENTS

| | | | |
|---|---|---|---|
| 5,442,169 A * | 8/1995 | Kunz | 250/227.21 |
| 6,239,909 B1 | 5/2001 | Hayashi et al. | |
| 6,483,950 B1 * | 11/2002 | Wallack | 382/285 |
| RE38,307 E | 11/2003 | Gustafsson et al. | |
| 7,342,717 B1 * | 3/2008 | Hausmann | C12Q 1/6869 359/368 |
| 9,146,393 B2 * | 9/2015 | Nomura | G02B 21/14 |
| 2002/0000507 A1 | 1/2002 | Engelhardt | |
| 2002/0044332 A1 * | 4/2002 | Engelhardt et al. | 359/285 |
| 2003/0021018 A1 | 1/2003 | Birk et al. | |
| 2004/0105485 A1 * | 6/2004 | Bures et al. | 374/142 |
| 2008/0158668 A1 * | 7/2008 | Ouchi et al. | 359/385 |
| 2009/0219607 A1 | 9/2009 | Saggau et al. | |
| 2010/0067103 A1 | 3/2010 | Sangu | |
| 2011/0036996 A1 * | 2/2011 | Wolleschensky | G01N 21/6458 250/459.1 |
| 2012/0098951 A1 * | 4/2012 | Borovytsky | G02B 21/06 348/79 |

FOREIGN PATENT DOCUMENTS

| | | |
|---|---|---|
| JP | A-2002-72160 | 3/2002 |
| JP | A-2003-66340 | 3/2003 |
| JP | A-2005-148497 | 6/2005 |
| JP | A-2010-197986 | 9/2010 |

OTHER PUBLICATIONS

Lukosz, "Optical Systems with Resolving Powers Exceeding the Classical Limit, II," *Journal of the Optical Society of America*, vol. 57, No. 7, pp. 932-941, published by Optical Society of America, Jul. 1967.

Gliko et al,, "Development of fast two-dimensional standing wave microscopy using acousto-optic deflectors," *Proc. of SPIE*, vol. 6861 68610B, pp. 1-8, Jan. 2008.

Jan. 24, 2012 International Search Report issued in International Application No. PCT/JP2011/005682 (with translation).

Model LS110A-XY: Dual Axis AO Deflector, retrieved Dec. 16, 2013 from www.isomet.com.

Feb. 4, 2014 Office Action issued in Japanese Patent Application No. 2012-538568 (with translation).

Gliko et al; "Development of fast two-dimensional standing wave microscopy using acousto-optic deflectors;" Proc. of SPIE; Jan. 2008; vol. 6861; 68610B-1-68610B-8.

Oct. 14, 2014 Office Action issued in Chinese Patent Application No. 201180049642.5.

* cited by examiner

STRUCTURED ILLUMINATION APPARATUS, STRUCTURED ILLUMINATION MICROSCOPY APPARATUS, AND PROFILE MEASURING APPARATUS

CROSS REFERENCE TO THE RELATED APPLICATIONS

This application is a continuation application of International Application PCT/JP2011/005682, filed Oct. 11, 2011, designating the U.S., and claims the benefit of priority from Japanese Patent Application No. 2010-231458 and Japanese Patent Application No. 2011-087068, filed on Oct. 14, 2010 and Apr. 11, 2011, respectively, the entire contents of which are incorporated herein by reference.

BACKGROUND

1. Field

The present application relates to a structured illumination apparatus, a structured illumination microscopy apparatus, and a pattern projection type profile measuring apparatus capable of realizing a super resolution in an in-plane direction.

2. Description of the Related Art

A super-resolution microscope is one that modulates an illumination light flux that illuminates a sample plane and demodulates an image-forming light flux which is incident on a position that is substantially conjugated with the sample plane of an image-forming optical system, in order to make information regarding a high spatial frequency that exceeds a resolution limit (diffracted light at a large angle) out of diffracted light that outgoes from a sample, to be contributed to an image formation (refer to Non-Patent Document 1: W. Lukosz, "Optical systems with resolving powers exceeding the classical limit. II", Journal of the Optical Society of America, Vol. 57, PP. 932, 1967; Patent Document 1: Japanese Unexamined Patent Application Publication No. H11-242189; Patent Document 2: Specification of U.S. Pat. No. RE 38307; Patent Document 3: U.S. Patent Application Publication No. 2009/0219607; and the like).

In a method of Non-Patent Document 1, a diffraction grating (diffraction grating for modulation) is disposed in the vicinity of a sample plane, and a diffraction grating (diffraction grating for demodulation) having a grating constant which is conjugated with that of the diffraction grating for modulation, is disposed at a position which is substantially conjugated with the sample plane of an image-forming optical system. When those two diffraction gratings are moved in a conjugated manner, it becomes possible to observe a structure of sample by separating it from patterns of the diffraction gratings.

Meanwhile, Patent Document 1 discloses an example in which a structured illumination microscope is applied to a fluorescent observation. In a method of Patent Document 1, a light flux that outgoes from a coherent light source is split into two light fluxes by a diffraction grating, and those two light fluxes are individually condensed on mutually different positions on a pupil of objective lens. At this time, the two light fluxes outgo from the objective lens as collimated light fluxes with different angles, and overlap each other on a sample plane to form striped interference fringes. Accordingly, the sample plane is subjected to structured illumination. Further, in the method of Patent Document 1, images of sample images are repeatedly obtained while shifting a phase of the structured illumination in steps, and calculation corresponding to the aforementioned separation (separating calculation) and calculation corresponding to the aforementioned demodulation (demodulating calculation) are performed on the obtained plurality of images.

Incidentally, as a method of shifting the phase of structured illumination in steps, there are a method in which a wedge-shaped prism is inserted into one of the above-described two light fluxes and moved in steps in a direction perpendicular to an optical axis, a method in which a diffraction grating is moved in steps in a direction perpendicular to a grid line, a method in which a sample is moved in steps in a pitch direction of structured illumination, and the like.

Further, in a method of Patent Document 2, images of sample images are repeatedly obtained while changing a direction of structured illumination in steps, to thereby achieve a super-resolution effect over various directions. Incidentally, as a method of changing the direction of structured illumination in steps, there is a method in which a diffraction grating or a sample is rotated in steps around an optical axis by a rotation motor or the like.

Particularly, in the method of Non-Patent Document 2: Olga Gliko et al., "Development of fast two-dimensional standing wave microscopy using acousto-optic deflectors", Proc. of SPIE Vol. 6861 68610B-8, four acousto-optical elements are used to change the direction or a phase of the structured illumination.

However, when an optical element is moved in steps, a certain period of time is required for stopping the moving optical element at an appropriate position, so that it is difficult, in the method of Patent Document 2, to reduce a period of time required to completely obtain the required images. Particularly, when a sample being an observational object is an organism specimen, there is a chance that a structure of the sample changes every second, so that the obtainment of images should be performed as fast as possible.

Further, in a method of using four acousto-optical elements as the method of Non-Patent Document 2, an optical system of a super-resolution microscope becomes complicated, and due to the complication of the system, there is a disadvantage in the aspect of the adjustment of the optical system and the cost.

Accordingly, the present application has a proposition to provide a structured illumination apparatus having a configuration suitable for increasing a speed of obtaining images, an efficient structured illumination microscopy apparatus, and an efficient profile measuring apparatus.

SUMMARY

A structured illumination apparatus of the present embodiment includes a light modulator being disposed in an exit flux of light from a light source and in which a sonic wave propagation path is arranged in a direction traversing the exit flux of light; a driving unit generating a sonic standing wave in the sonic wave propagation path by giving a driving signal for vibrating a medium of the sonic wave propagation path to the light modulator; and an illuminating optical system making mutually different diffracted components of the exit flux of light passed through the sonic wave propagation path to be interfered with each other, and forming interference fringes of the diffracted components on an observational object.

Note that the driving unit may generate the sonic standing wave by setting a frequency of the driving signal given to the light modulator to a predetermined frequency.

Further, the structured illumination apparatus of the present embodiment may include an adjusting unit adjusting at least one of the frequency and an amplitude of the driving signal in accordance with a temperature of the medium of the sonic wave propagation path.

Further, the structured illumination apparatus of the present embodiment may include a temperature sensor detecting the temperature of the medium of the sonic wave propagation path in which the adjusting unit adjusts the frequency of the driving signal in accordance with the temperature being detected by the temperature sensor.

Further, the structured illumination apparatus of the present embodiment may include a temperature sensor detecting the temperature of the medium of the sonic wave propagation path in which the adjusting unit adjusts the amplitude of the driving signal in accordance with the temperature being detected by the temperature sensor.

Further, the structured illumination apparatus of the present embodiment may include a heat releasing unit releasing heat being generated in the medium of the sonic wave propagation path.

Further, the structured illumination apparatus of the present embodiment may include a phase shifting unit shifting a phase of the interference fringes.

Further, the phase shifting unit may be a driving device moving the light modulator in a predetermined direction.

Further, the driving device may change a movement amount in accordance with a direction of the sonic standing wave.

Further, the exit flux of light being effective and contributing to the interference fringes may be the exit flux of light passed through a predetermined partial area separated from both ends of the sonic wave propagation path, and the phase shifting unit may be the driving unit which shifts the phase of the interference fringes by changing a wavelength of the sonic standing wave in a predetermined pattern.

Further, the driving unit may change the wavelength of the sonic standing wave by changing the frequency of the driving signal given to the light modulator in a predetermined pattern.

Further, the driving unit may change the frequency in a pattern in which a total wave number of the sonic standing wave is changed by M/2 (where |M| is an integer of 1 or more), and when a phase shift amount of the interference fringes is set to $\Delta_\psi$, a distance D from either end portion of the sonic wave propagation path to the partial area and a total length L of the sonic wave propagation path may be set to satisfy a relation of D:L=$\Delta_\psi$/M:2π.

Further, it may be M=1. Further, it may be $\Delta_\psi$=2π/k (where |k| is an integer of 2 or more).

Further, the light modulator may have a plurality of the sonic wave propagation path which intersects at the partial area.

Further, the light modulator may include a prismatic acousto-optical medium having a plurality of mutually opposing parallel coupled side faces, and a plurality of ultrasonic wave transducers each generating a sonic standing wave in the sonic wave propagation path formed between each of the plurality of coupled side faces.

Further, a disposition relation of the plurality of the sonic wave propagation path may be set to make a direction of the interference fringes to be switchable among mutually different plurality of directions in a plane orthogonal to an optical axis of the illuminating optical system.

Further, the structured illumination apparatus of the present embodiment may include a signal generating unit generating the driving signal given to any one of the plurality of ultrasonic wave transducers, and a switching unit switching an input destination of the driving signal being generated by the signal generating unit among the plurality of ultrasonic wave transducers.

Further, a structured illumination microscopy apparatus of the present embodiment includes any one of the structured illumination apparatuses of the present embodiment; and an image-forming optical system forming, on a detector, an image with observational light flux from the observational object illuminated by the structured illumination apparatus.

Further, the structured illumination microscopy apparatus of the present embodiment may include an adjusting unit adjusting an exposure amount of the detector in accordance with the temperature of the medium of the sonic wave propagation path.

Further, the observational light flux may be a fluorescent light flux.

Further, the structured illumination microscopy apparatus of the present embodiment may include a calculating unit calculating a super-resolved image of the observational object based on a plurality of images sequentially obtained by the detector during a switching of the wavelengths.

Further, a profile measuring apparatus of the present embodiment includes any one of the structured illumination apparatuses of the present embodiment; an image detector detecting an image of the observational object illuminated by the structured illumination apparatus; and a calculating unit calculating a profile of the observational object based on a plurality of images sequentially obtained by the image detector during a switching of the wavelengths.

DETAILED DESCRIPTION OF THE EMBODIMENTS

First Embodiment

Hereinafter, a first embodiment of the present invention will be described by using the drawings. The present embodiment is an embodiment of a structured illuminating microscopy system which is applied to a fluorescent observation.

Figure 1:
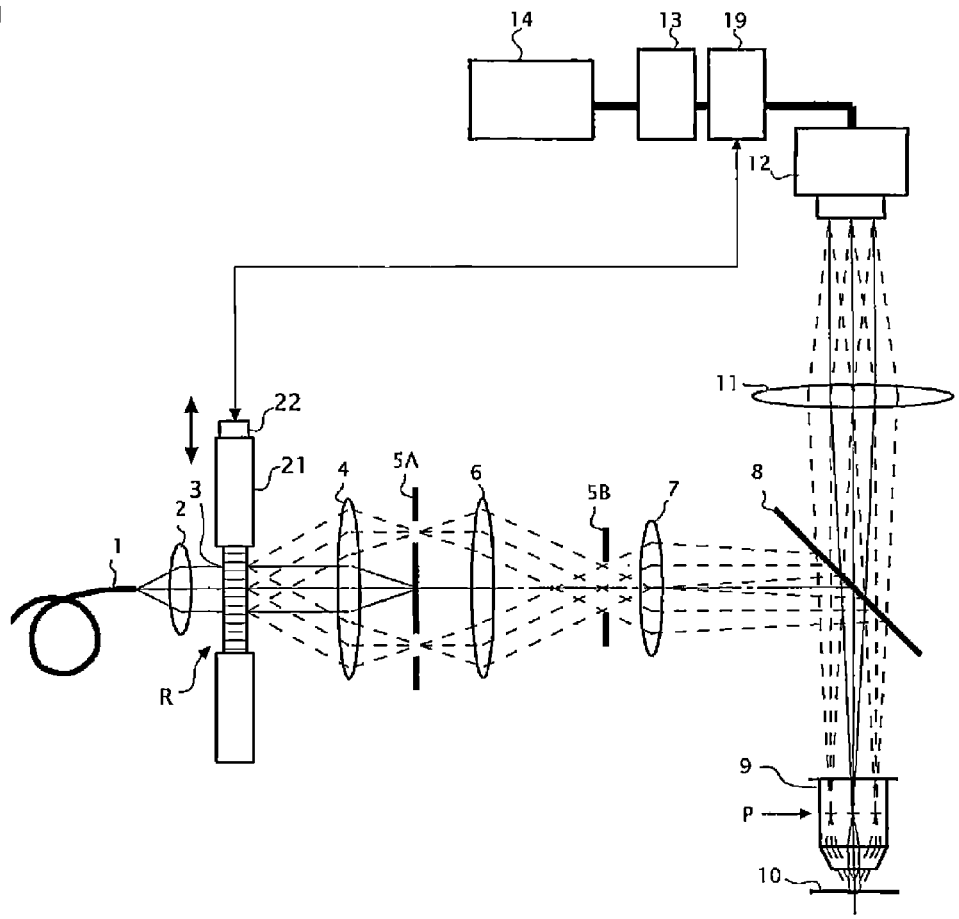
FIG. 1 is a configuration diagram of a structured illuminating microscopy system of a first embodiment.

FIG. 1 is a configuration diagram of a structured illuminating microscopy system of the present embodiment. As illustrated in FIG. 1, in the structured illuminating microscopy system, there are disposed an optical fiber 1, a collector lens 2, an ultrasonic wave light modulator 3, a lens 4, a 0th-order light blocking mask 5A, a lens 6, a field stop 5B, a lens 7, dichroic mirror 8, a second objective lens 11, an imaging device (CCD camera or the like) 12, a controlling device 19, an image storing-calculating device (computer or the like) 13, an image displaying device 14, an objective lens 9 and the like. A reference numeral 10 in FIG. 1 denotes an observational object plane (specimen plane) of a specimen placed on a not-illustrated stage, and the specimen is a fluorescent-stained organism specimen.

In FIG. 1, the optical fiber 1 guides light from a not-illustrated coherent light source, and forms, at an emission end thereof, a secondary point light source (coherent secondary point light source). Note that a wavelength of the not-illustrated coherent light source is set to the same wavelength as an excitation wavelength of the specimen. The light outgone from the secondary point light source is converted into collimated light by the collector lens 2 to be incident on the ultrasonic wave light modulator 3.

The ultrasonic wave light modulator 3 has an ultrasonic wave propagation path R propagating an ultrasonic wave in a direction perpendicular to an optical axis, and gives, by generating a planar standing wave of ultrasonic wave (referred to as "ultrasonic standing wave", hereinafter) in the ultrasonic wave propagation path R, a refractive index distribution of sinusoidal shape to the ultrasonic wave propagation path R. Such an ultrasonic wave light modulator 3 operates as a phase type diffraction grating with respect to the incident light, and branches the light into diffracted lights of respective orders. In FIG. 1, a solid line indicates 0th-order diffracted light, and a dotted line indicates ±first-order diffracted light.

Note that the ultrasonic wave light modulator 3 is supported, by a supporting frame 21, from a peripheral edge thereof, and to the supporting frame 21, there is provided a piezoelectric actuator 22 that displaces the supporting frame 21 and the ultrasonic wave light modulator 3 in a direction perpendicular to a wavefront of the ultrasonic wave. Incidentally, a stroke corresponding to one step of the piezoelectric actuator 22 is set to a value at which a phase of structured illumination to be described later is shifted by $2\pi/3$.

The diffracted lights of respective orders outgone from the ultrasonic wave light modulator 3 pass through the lens 4, and then form a pupil conjugate plane. In the vicinity of the pupil conjugate plane, the 0th-order light blocking mask 5A is disposed, and the mask has a function of blocking 0th-order diffracted light and high-order diffracted light of second-order or higher, and making only ±first-order diffracted light pass through the mask.

The ±first-order diffracted lights passed through the 0th-order light blocking mask 5A pass through the lens 6, and then form a specimen conjugate plane. In the vicinity of the specimen conjugate plane, the field stop 5B is disposed, and the field stop 5B has a function of controlling a size of illuminated area (observational area) on a specimen plane 10.

The ±first-order diffracted lights passed through the field stop 5B pass through the lens 7, and after that, the lights are incident on the dichroic mirror 8 and reflected by the dichroic mirror 8. The ±first-order diffracted lights reflected by the dichroic mirror 8 respectively form spots at mutually different positions on a pupil P of the objective lens 9. Note that the formation positions of the two spots on the pupil P are at approximately an outermost peripheral portion of the pupil P, and positions symmetric to each other with respect to an optical axis of the objective lens 9.

Therefore, the ±first-order diffracted lights outgone from the tip of the objective lens 9 illuminate the specimen plane 10 from mutually opposing directions at an angle corresponding to NA of the objective lens 9. As described above, these ±first-order diffracted lights are mutually coherent lights, so that striped interference fringes with a uniform fringe pitch are projected onto the specimen plane 10. Accordingly, an illumination pattern of the specimen plane 10 corresponds to an illumination pattern having a fringe structure. The illumination with the illumination pattern having the fringe structure as above is structured illumination. In the fluorescent area of the specimen plane 10 subjected to the structured illumination, a fluorescent material is excited to generate fluorescence.

Note that in order to form the illumination pattern having the fringe structure on the specimen plane 10 at high contrast, it is required that all of the ±first-order diffracted lights which are incident on the specimen plane 10 have S-polarized light with respect to an electric field vibration direction perpendicular to a plane of incidence, namely, the specimen plane 10. In order to realize that, it is desirable to prepare either of the following two types of optical systems (a first optical system, a second optical system).

As the first optical system, not-illustrated polarizer and first ¼ wavelength plate are provided between the collector lens 2 and the ultrasonic wave light modulator 3, and further, a not-illustrated second ¼ wavelength plate is provided in the vicinity of the 0th-order light blocking mask 5A in FIG. 1. When the first optical system is employed, light that transmits through the ultrasonic wave light modulator 3 is made to be circularly polarized light by the first ¼ wavelength plate disposed in the vicinity of the ultrasonic wave light modulator 3, and light after being transmitted through the 0th-order light blocking mask 5A becomes linearly polarized light. Further, by rotating the second ¼ wavelength plate disposed in the vicinity of the light blocking mask 5A, it is possible to obtain polarized light in a desired direction.

As the second optical system, a not-illustrated polarizer is provided between the collector lens 2 and the ultrasonic wave light modulator 3, and a not-illustrated ½ wavelength plate is provided in the vicinity of the 0th-order light blocking mask 5A in FIG. 1. When the second optical system is employed, light that transmits through the ultrasonic wave light modulator 3 is made to be linearly polarized light in a specific direction by the polarizer disposed in the vicinity of the ultrasonic wave light modulator 3, and light after being transmitted through the 0th-order light blocking mask 5A becomes linearly polarized light whose direction is different from the direction of the linearly polarized light transmitted through the ultrasonic wave light modulator 3. Further, by rotating the ½ wavelength plate disposed in the vicinity of the light blocking mask 5A, it is possible to obtain polarized light in a desired direction.

Here, when the structured illumination is employed, a moiré fringe corresponding to a difference between a structure period of the structured illumination and a structure period of the fluorescent area appears on the specimen plane 10. On the moiré fringe, a spatial frequency of the structure of the fluorescent area is modulated to be shifted to a spatial frequency that is lower than the actual spatial frequency. Therefore, with the use of the structured illumination, even a fluorescence that exhibits a high component of spatial frequency in the structure of the fluorescent area, namely, a fluorescence emitted at a large angle that exceeds a resolution limit of the objective lens 9, can be incident on the objective lens 9.

The fluorescence that is emitted from the specimen plane 10 and incident on the objective lens 9 is converted into collimated light by the objective lens 9, and then incident on the dichroic mirror 8. The fluorescence transmits through the dichroic mirror 8, and then passes through the second objective lens 11, to thereby form a fluorescent image of the specimen plane 10 on an imaging plane of the imaging device 12. Note that this fluorescent image includes not only structure information of the fluorescent area of the specimen plane 10 but also structure information of the structured illumination, and in this fluorescent image, the spatial frequency of the structure of the fluorescent area of the specimen plane 10 is still being modulated (namely, the spatial frequency is still being shifted to the spatial frequency that is lower than the actual spatial frequency).

The controlling device 19 displaces the aforementioned piezoelectric actuator 22, to thereby move the position of the ultrasonic wave light modulator 3 in steps in three ways, to a reference position and two positions at both sides of the reference position. Accordingly, a phase of the structured illumination is shifted by one period. Further, the controlling device 19 drives the imaging device 12 when the ultrasonic wave light modulator 3 is at the positions of respective steps to obtain three types of image data $I_1$, $I_2$, and $I_3$, and sequentially sends those pieces of image data $I_1$, $I_2$, and $I_3$ to the image storing-calculating device 13. Note that although the three types of image data with different phases of structured illumination are obtained in this case, it is also possible to obtain four types or more of image data with different phases of structured illumination. However, it is required to obtain three types of image data, at the minimum, in order to enable the performance of separating calculation (which will be described later) by the image storing-calculating device 13.

The image storing-calculating device 13 performs separating calculation on the pieces of image data $I_1$, $I_2$, and $I_3$ which are taken therein, to thereby obtain image data I as a result of removing the structure information of structured illumination. Further, the image storing-calculating device 13 performs demodulating calculation on the image data I to obtain image data I' as a result of returning the spatial frequency of the structure information of the fluorescent area to the actual spatial frequency, and sends the image data I' to the image displaying device 14. Therefore, a resolved image that exceeds the resolution limit of the objective lens 9 (super-resolved image) is displayed on the image displaying device 14.

Figure 2:
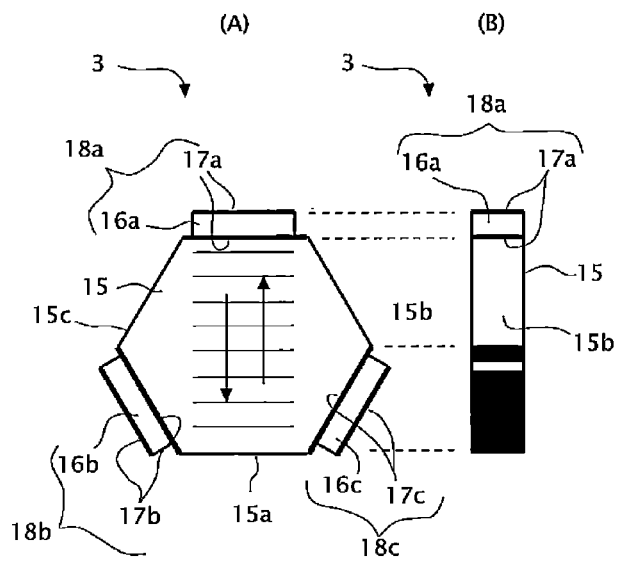
FIG. 2 is configuration diagrams of an ultrasonic wave light modulator 3.

FIG. 2 is configuration diagrams of the ultrasonic wave light modulator 3. FIG. 2(A) is a diagram in which the ultrasonic wave light modulator 3 is seen from the front (optical axis direction), and FIG. 2(B) is a diagram in which the ultrasonic wave light modulator 3 is seen from the side (direction perpendicular to the optical axis).

As illustrated in FIG. 2, the ultrasonic wave light modulator 3 has an acousto-optical medium 15 having a regular hexagonal prism shape and having a central axis arranged on the optical axis, and three transducers 18a, 18b, and 18c individually provided on three side faces which are not opposed to one another, out of six side faces of the acousto-optical medium 15. Note that a material of the acousto-optical medium 15 is, for example, a quartz glass, a tellurite glass, a dense flint glass, a flint glass or the like, and the six side faces and two bottom faces of the acousto-optical medium are respectively polished with sufficient precision.

The transducer 18a is an ultrasonic wave transducer having a piezoelectric body 16a and two electrodes 17a individually formed on upper and lower faces of the piezoelectric body 16a, and is joined to one side face of the acousto-optical medium 15 via the electrode 17a being one of the two electrodes 17a.

Therefore, when an AC voltage of high frequency is applied between the two electrodes 17a of the transducer 18a, the piezoelectric body 16a vibrates in a thickness direction, resulting in that a planar ultrasonic wave propagates from a formation face of the transducer 18a toward a side face 15a which opposes the formation face, and the ultrasonic wave turns back the optical path at the side face 15a. Accordingly, when the frequency of AC voltage applied between the two electrodes 17a is set to a specific frequency, the ultrasonic wave becomes a standing wave.

At this time, to a refractive index in the inside of the acousto-optical medium 15, a distribution of sinusoidal shape is given in a traveling direction of the ultrasonic wave. Therefore, the ultrasonic wave light modulator 3 in this state becomes a phase type diffraction grating having a phase grating parallel to the side face 15a. Hereinafter, a direction of modulation of the ultrasonic wave light modulator 3 in this state (direction of arrow mark in FIG. 2) is referred to as a "first direction".

Note that when the ultrasonic wave formed in the inside of the acousto-optical medium 15 is deviated from a perfect standing wave, the diffraction efficiency of the ±first-order diffracted light described above is lowered, resulting in that the contrast of the structured illumination is lowered. This is because, when the ultrasonic wave light modulator 3 is in a driven state, the acousto-optical medium 15 generates heat due to Joule heat in the piezoelectric body 16a, a reflection of sonic wave at the joint portion, an attenuation of sonic wave in the acousto-optical medium 15 and the like, and the medium expands, so that the characteristic of the medium changes with time. For this reason, even if the ultrasonic wave light modulator 3 is started to be driven at a certain frequency, and a standing wave stands in an initial state, there is a possibility that, as time passes, a chance of satisfying a condition in which the standing wave stands is eliminated. Specifically, the frequency at which the standing wave stands (appropriately frequency) depends on a temperature of the ultrasonic wave light modulator 3.

However, as long as an amount of decrease in the contrast falls within an allowable range (namely, a calculation error of the above-described calculation falls within the allowable range), the ultrasonic wave formed in the inside of the acousto-optical medium 15 may be deviated in some degree from the perfect standing wave. Accordingly, in this case, there is no problem to construe the "appropriately frequency" as a "range of frequency in the vicinity of the frequency at which the standing wave stands and by which the calculation error can be fallen within the allowable range".

Further, the transducer 18b, which also has the same configuration as that of the transducer 18a, has a piezoelectric body 16b and two electrodes 17b individually formed on upper and lower faces of the piezoelectric body 16b, and is joined to one side face of the acousto-optical medium 15 via the electrode 17b being one of the two electrodes 17b.

Therefore, when an AC voltage of appropriately frequency is applied between the two electrodes 17b of the transducer 18b, the acousto-optical medium 15 becomes a phase type diffraction grating having a phase grating parallel to the formation face of the transducer 18b and a side face 15b that opposes the formation face. Hereinafter, a direction of modulation of the ultrasonic wave light modulator 3 in this state (direction of grating pitch) is referred to as a "second direction". This second direction makes an angle of 60° with the first direction.

Further, the transducer 18c, which also has the same configuration as that of the transducer 18a, has a piezoelectric body 16c and two electrodes 17c individually formed on upper and lower faces of the piezoelectric body 16c, and is joined to one side face of the acousto-optical medium 15 via the electrode 17c being one of the two electrodes 17c.

Therefore, when an AC voltage of appropriately frequency is applied between the two electrodes 17c of the transducer 18c, the acousto-optical medium 15 becomes a phase type diffraction grating having a phase grating parallel to the formation face of the transducer 18c and a side face 15c that opposes the formation face. Hereinafter, a direction of modulation of the ultrasonic wave light modulator 3 in this state (direction of grating pitch) is referred to as a "third direction". This third direction makes an angle of −60° with the first direction.

Figure 3:
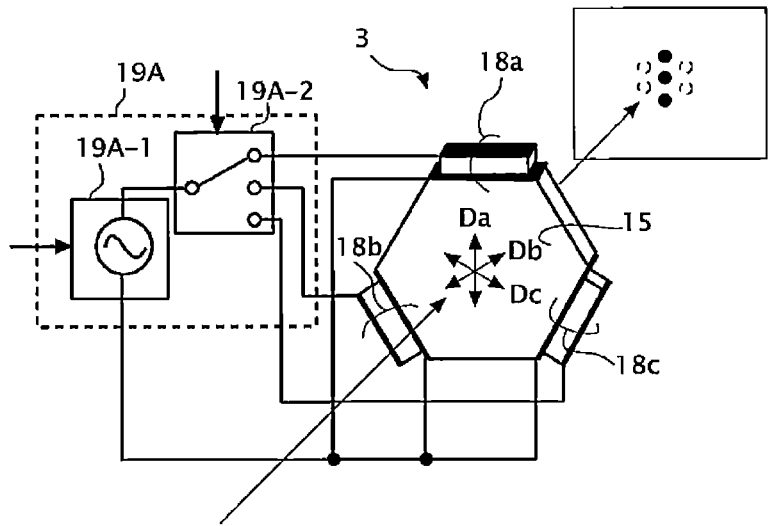
FIG. 3 is a diagram explaining a driving circuit 19A of the ultrasonic wave light modulator 3.

FIG. 3 is a diagram explaining a driving circuit 19A of the ultrasonic wave light modulator 3. Hereinafter, explanation will be made by setting that this driving circuit 19A is a part of the controlling device 19 illustrated in FIG. 1.

As illustrated in FIG. 3, the driving circuit 19A includes a high-frequency AC power source 19A-1 and a selector switch 19A-2.

The high-frequency AC power source 19A-1 generates an AC voltage to be supplied to the ultrasonic wave light modulator 3. A frequency of the AC voltage is about several tens of MHz to 100 MHz, and is controlled to an appropriate value by the CPU in the controlling device 19.

The selector switch 19A-2 is disposed between the high-frequency AC power source 19A-1 and the ultrasonic wave light modulator 3, and can switch a connection destination on the side of the ultrasonic wave light modulator 3, among the three transducers 18a, 18b, and 18c of the ultrasonic wave light modulator 3. The connection destination of the switch 19A-2 is appropriately switched by the CPU in the controlling device 19.

When the connection destination of the selector switch 19A-2 is on the side of the transducer 18a, the AC voltage is applied between the two electrodes of the transducer 18a, so that the direction of modulation of the ultrasonic wave light modulator 3 becomes a first direction Da.

Further, when the connection destination of the selector switch 19A-2 is on the side of the transducer 18b, the AC voltage is applied between the two electrodes of the transducer 18b, so that the direction of modulation of the ultrasonic wave light modulator 3 becomes a second direction Db.

Further, when the connection destination of the selector switch 19A-2 is on the side of the transducer 18c, the AC voltage is applied between the two electrodes of the transducer 18c, so that the direction of modulation of the ultrasonic wave light modulator 3 becomes a third direction Dc.

Therefore, the CPU in the controlling device 19 can switch the direction of modulation of the ultrasonic wave light modulator 3 among the first direction Da, the second direction Db, and the third direction Dc, only by switching the connection destination of the selector switch 19A-2.

Note that a relation among a direction of structured illumination when the direction of modulation of the ultrasonic wave light modulator 3 is the first direction Da, a direction of structured illumination when the direction of modulation of the ultrasonic wave light modulator 3 is the second direction Db, and a direction of structured illumination when the direction of modulation of the ultrasonic wave light modulator 3 is the third direction Dc, is the same as a relation among the first direction Da, the second direction Db, and the third direction Dc.

Therefore, in the description hereinbelow, the direction of structured illumination when the direction of modulation of the ultrasonic wave light modulator 3 is the first direction Da is referred to as a "first direction Da", the direction of structured illumination when the direction of modulation of the ultrasonic wave light modulator 3 is the second direction Db is referred to as a "second direction Db", and the direction of structured illumination when the direction of modulation of the ultrasonic wave light modulator 3 is the third direction Dc is referred to as a "third direction Dc".

Figure 4:
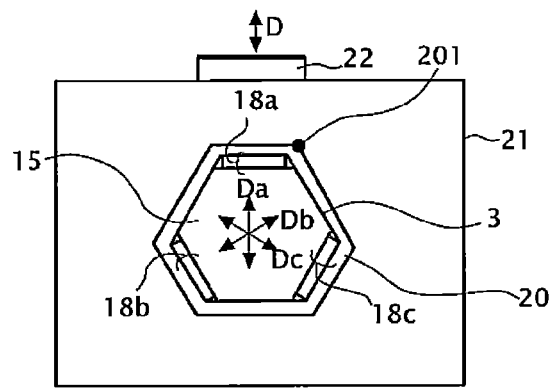
FIG. 4 is a diagram in which a periphery of the ultrasonic wave light modulator 3 is seen from an optical axis direction.

FIG. 4 is a diagram in which a periphery of the ultrasonic wave light modulator 3 is seen from the optical axis direction.

As illustrated in FIG. 4, a direction D in which the piezoelectric actuator 22 is displaced coincides with the first direction Da. Therefore, if the piezoelectric actuator 22 is displaced in the direction D when the direction of structured illumination is Da, a phase of the structured illumination is of course shifted.

However, each of an angle made by the direction D and the second direction Db, and an angle made by the direction D and the third direction Dc is not 90°, so that even if the direction of structured illumination is the second direction Db or the third direction Dc, when the piezoelectric actuator 22 is displaced in the direction D, the phase of the structured illumination is shifted.

Note that when the stroke corresponding to one step of the piezoelectric actuator 22 is made to be unchanged, an amount of phase shift corresponding to one step of the structured illumination when the direction of structured illumination is the first direction Da and that when the direction of structured illumination is not the first direction Da, become different.

Therefore, the CPU in the controlling device 19 switches, when the direction of structured illumination is switched among the first direction Da, the second direction Db, and the third direction Dc, the stroke corresponding to one step of the piezoelectric actuator 22 (namely, a value of voltage applied to the piezoelectric actuator 22).

Concretely, the CPU first sets a stroke $\Delta$ corresponding to one step of the piezoelectric actuator 22 when the direction of structured illumination is the first direction Da, to a value at which a phase of the structured illumination is shifted by $2\pi/3$.

Further, the CPU sets a stroke corresponding to one step of the piezoelectric actuator 22 when the direction of structured illumination is the second direction Db to $2\Delta$, and sets a stroke corresponding to one step of the piezoelectric actuator 22 when the direction of structured illumination is the third direction Dc to $-2\Delta$.

Figure 5:
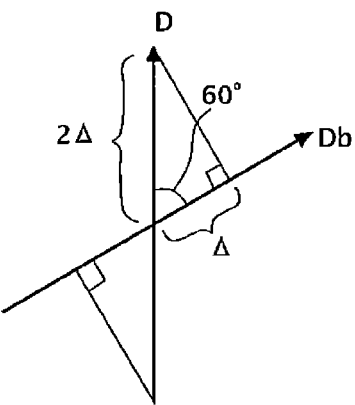
FIG. 5 is a diagram explaining a stroke corresponding to one step of a piezoelectric actuator 22 when a direction of structured illumination is a second direction Db.

As illustrated in FIG. 5, the direction D and the second direction Db make an angle of 60°, so that when the stroke $2\Delta$ in the direction D is projected in the second direction Db, a relation of $1\Delta \times \cos 60° = \Delta$ is satisfied. Accordingly, when the stroke in the direction D is set to $2\Delta$, the stroke in the second direction Db becomes $\Delta$.

Therefore, according to this setting, the amount of phase shift corresponding to one step when the direction of structured illumination is the second direction Db coincides with the amount of phase shift corresponding to one step when the direction of structured illumination is the first direction Da.

Figure 6:
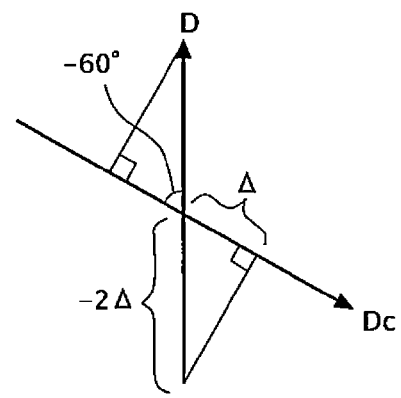
FIG. 6 is a diagram explaining a stroke corresponding to one step of the piezoelectric actuator 22 when a direction of structured illumination is a third direction Dc.

Further, as illustrated in FIG. 6, the direction D and the third direction Dc make an angle of $-60°$, so that when the stroke $-2\Delta$ in the direction D is projected in the third direction Dc, a relation of $-2\Delta \times \cos(-60°) = \Delta$ is satisfied. Accordingly, when the stroke in the direction D is set to $-2\Delta$, the stroke in the third direction Dc becomes $\Delta$.

Therefore, according to this setting, the amount of phase shift corresponding to one step when the direction of structured illumination is the third direction Dc coincides with the amount of phase shift corresponding to one step when the direction of structured illumination is the first direction Da.

As a result of the above, the amount of phase shift corresponding to one step of the structured illumination is kept constant ($2\pi/3$, in this case), regardless of the direction of structured illumination.

Further, as illustrated in FIG. 4, a plastic pad 20 is interposed between the ultrasonic wave light modulator 3 and the supporting frame 21, and a temperature sensor 201 configured by a platinum resistor or the like, for example, is provided between the pad 20 and the supporting frame 21. A detection target of the temperature sensor 201 is a temperature of the ultrasonic wave light modulator 3 ($\approx$ temperature of the acousto-optical medium 15). The temperature detected by the temperature sensor 201 is referred to by the CPU in the controlling device 19 at an appropriate timing, for the purpose of keeping a frequency of the above-described AC voltage to the appropriately frequency (frequency at which the standing wave stands).

Figure 7:
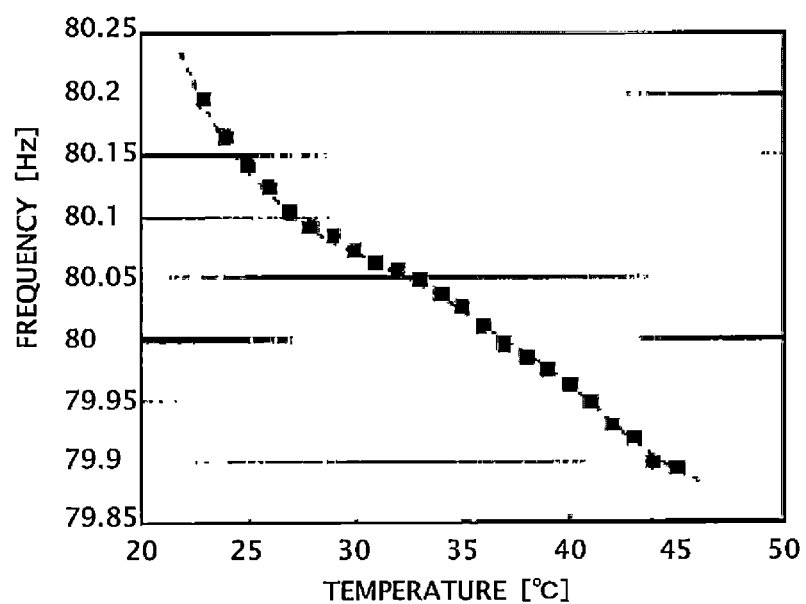
FIG. 7 is a graph illustrating a relation between a temperature of the ultrasonic wave light modulator 3 and an appropriately frequency.

FIG. 7 is a graph illustrating a relation between the temperature of the ultrasonic wave light modulator 3 and the appropriately frequency (appropriately frequency information). As illustrated in FIG. 7, when the temperature of the ultrasonic wave light modulator 3 is changed from about 25° C. to about 45° C., the appropriately frequency is changed from about 80.2 MHz to about 79.9 MHz.

Therefore, the CPU in the controlling device 19 previously stores the appropriately frequency information in a form of look-up table. In the look-up table, respective temperatures of the acousto-optical medium 15 and appropriately frequencies at the respective temperatures are stored in a state of being mutually corresponded.

Figure 8:
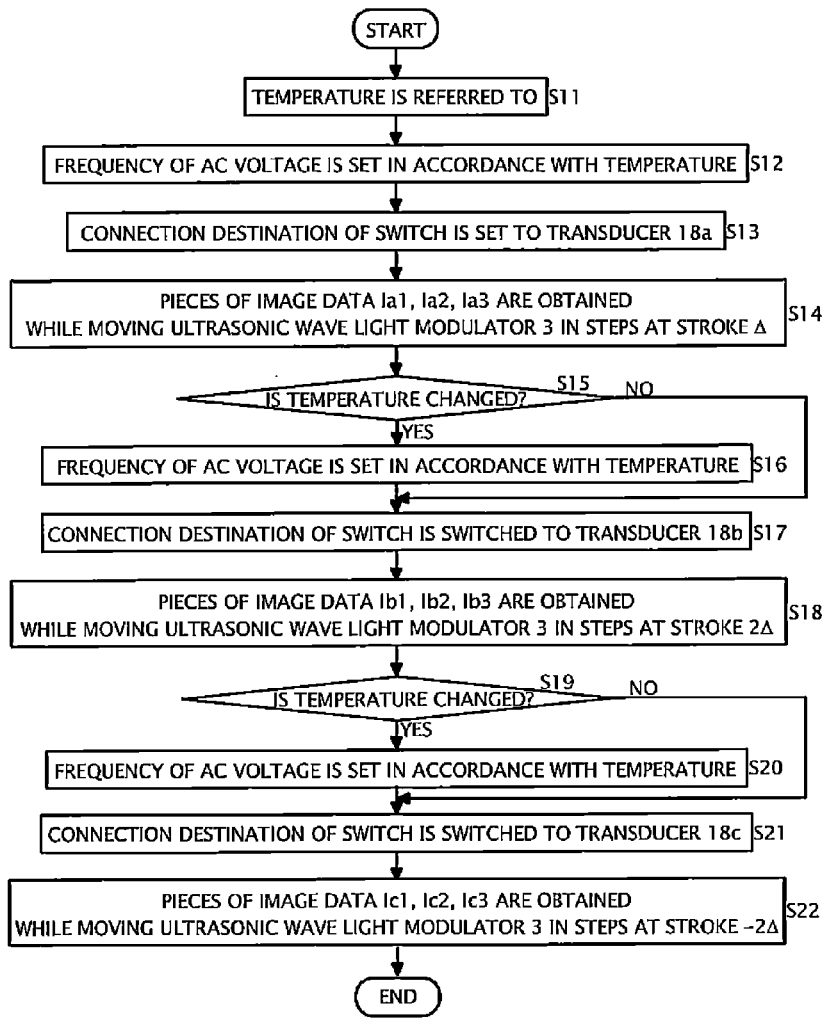
FIG. 8 is an operational flow chart of a CPU in the first embodiment.

FIG. 8 is an operational flow chart of the CPU in the first embodiment. Hereinafter, respective steps will be described in order.

Step S11: The CPU refers to a temperature T which is detected by the temperature sensor 201.

Step S12: The CPU refers to the look-up table in accordance with the temperature T, and reads an appropriately frequency f which is corresponded to the temperature T, as an appropriately frequency at the present moment. Further, the CPU sets a frequency of AC voltage generated by the high-frequency AC power source 19A-1, to the appropriately frequency f.

Step S13: The CPU sets the connection destination of the selector switch 19A-2 to the side of the transducer 18a, to thereby set the direction of structured illumination to the first direction Da.

Step S14: The CPU sets the stroke corresponding to one step of the piezoelectric actuator 22 to $\Delta$. Subsequently, the CPU drives the imaging device 12 in a state where the displacement of the piezoelectric actuator 22 is zero, and obtains image data $Ia_1$. Next, the CPU changes the displacement of the piezoelectric actuator 22 by one step toward a plus side, and then drives the imaging device 12 to obtain image data $Ia_2$. Subsequently, the CPU displaces the piezoelectric actuator 22 by two steps toward a minus side, and then drives the imaging device 12 to obtain image data $Ia_3$. Thereafter, the CPU returns the displacement of the piezoelectric actuator 22 to zero.

Note that the CPU in the present step controls a driving timing of the piezoelectric actuator 22 and a driving timing of the imaging device 12 via a not-illustrated synchronized controlling circuit, to thereby continuously obtain the necessary pieces of image data $Ia_1$, $Ia_2$, and $Ia_3$. Accordingly, a speed of obtaining the series of three pieces of image data $Ia_1$, $Ia_2$, and $Ia_3$ is kept to a high speed.

Step S15: The CPU refers to a temperature T which is detected by the temperature sensor 201, and judges whether or not the temperature T is different from the previous value. When the temperature T and the previous value are different, the process proceeds to step S16, and when they are the same, the process proceeds to step S17.

Step S16: The CPU refers to the look-up table in accordance with the temperature T, and reads an appropriately frequency f which is corresponded to the temperature T, as an appropriately frequency at the present moment. Further, the CPU sets a frequency of AC voltage generated by the high-frequency AC power source 19A-1, to the appropriately frequency f.

Step S17: The CPU switches the connection destination of the selector switch 19A-2 to the side of the transducer 18b, to thereby switch the direction of structured illumination to the second direction Db.

Step S18: The CPU switches the stroke corresponding to one step of the piezoelectric actuator 22 to $2\Delta$. Subsequently, the CPU sets the displacement of the piezoelectric actuator 22 to zero, and then drives the imaging device 12 to obtain image data $Ib_1$. Next, the CPU changes the displacement of the piezoelectric actuator 22 by one step toward the plus side, and then drives the imaging device 12 to obtain image data $Ib_2$. Subsequently, the CPU displaces the piezoelectric actuator 22 by two steps toward the minus side, and then drives the imaging device 12 to obtain image data $Ib_3$. Thereafter, the CPU returns the displacement of the piezoelectric actuator 22 to zero.

Note that the CPU in the present step controls a driving timing of the piezoelectric actuator 22 and a driving timing of the imaging device 12 via the not-illustrated synchronized controlling circuit, to thereby continuously obtain the necessary pieces of image data $Ib_1$, $Ib_2$, and $Ib_3$. Accordingly, a speed of obtaining the series of three pieces of image data $Ib_1$, $Ib_2$, and $Ib_3$ is kept to a high speed.

Step S19: The CPU refers to a temperature T which is detected by the temperature sensor 201, and judges whether or not the temperature T is different from the previous value. When the temperature T and the previous value are different, the process proceeds to step S20, and when they are the same, the process proceeds to step S21.

Step S20: The CPU refers to the look-up table in accordance with the temperature T, and reads an appropriately frequency f which is corresponded to the temperature T, as an appropriately frequency at the present moment. Further, the CPU sets a frequency of AC voltage generated by the high-frequency AC power source 19A-1, to the appropriately frequency f.

Step S21: The CPU switches the connection destination of the selector switch 19A-2 to the side of the transducer 18c, to thereby switch the direction of structured illumination to the third direction Dc.

Step S22: The CPU switches the stroke corresponding to one step of the piezoelectric actuator 22 to −2Δ. Subsequently, the CPU sets the displacement of the piezoelectric actuator 22 to zero, and then drives the imaging device 12 to obtain image data $Ic_1$. Subsequently, the CPU moves the piezoelectric actuator 22 by one step toward the plus side, and then drives the imaging device 12 to obtain image data $Ic_2$. Next, the CPU moves the piezoelectric actuator 22 by two steps toward the minus side, and then drives the imaging device 12 to obtain image data $IC_3$. Thereafter, the CPU returns the displacement of the piezoelectric actuator 22 to zero, and the flow is terminated.

Note that the CPU in the present step controls a driving timing of the piezoelectric actuator 22 and a driving timing of the imaging device 12 via the not-illustrated synchronized controlling circuit, to thereby continuously obtain the necessary pieces of image data $Ic_1$, $Ic_2$, and $Ic_3$. Accordingly, a speed of obtaining the series of three pieces of image data $Ic_1$, $Ic_2$, and $Ic_3$ is kept to a high speed.

Thereafter, the series of nine pieces of image data $Ia_1$, $Ia_2$, $Ia_3$, $Ib_1$, $Ib_2$, $Ib_3$, $Ic_1$, $Ic_2$, and $Ic_3$ obtained through the above-described flow are taken into the image storing-calculating device 13.

The image storing-calculating device 13 performs separating calculation with the use of linear calculation on the series of three pieces of image data $Ia_1$, $Ia_2$, and $Ia_3$, to obtain image data Ia including no structure information of the structured illumination, and performs demodulating calculation with the use of multiplication with a demodulation coefficient on the image data Ia, to obtain demodulated image data Ia' of super-resolved image along the first direction Da.

Further, the image storing-calculating device 13 performs separating calculation with the use of linear calculation on the series of three pieces of image data $Ib_1$, $Ib_2$, and $Ib_3$, to obtain image data Ib including no structure information of the structured illumination, and performs demodulating calculation with the use of multiplication with a demodulation coefficient on the image data Ib, to obtain demodulated image data Ib' of super-resolved image along the second direction Db.

Further, the image storing-calculating device 13 performs separating calculation with the use of linear calculation on the series of three pieces of image data $Ic_1$, $Ic_2$, and $Ic_4$, to obtain image data Ic including no structure information of the structured illumination, and performs demodulating calculation with the use of multiplication with a demodulation coefficient on the image data Ic, to obtain demodulated image data Ic' of super-resolved image along the third direction Dc.

Further, the image storing-calculating device 13 combines the three pieces of demodulated image data Ia', Ib', and Ic' on a wave number space, then returns the resultant to the real space again to obtain image data I of super-resolved image along the first direction Da, the second direction Db, and the third direction Dc, and sends the image data to the image displaying device 14. Therefore, the super-resolved image representing the structure of the fluorescent area of the specimen plane 10 in detail, is displayed on the image displaying device 14.

Here, in the above-described steps S13, S17, and S21, the direction of structured illumination is switched, and in the switching, it is only required to electrically change the connection state of the selector switch 19A-2, so that a period of time required for the switching is short, and can be reduced to 10 ms or less even including a time constant of the circuit system including the power source.

Further, in the above-described steps S11, S12, S15, S16, S19, and S20, the frequency of AC voltage is adjusted in accordance with the temperature of the ultrasonic wave light modulator 3, and a period of time required for the adjustment is extremely short as well.

Therefore, a period of time required for obtaining the series of nine pieces of image data $Ia_1$, $Ia_2$, $Ia_3$, $Ib_1$, $Ib_2$, $Ib_3$, $Ic_1$, $Ic_2$, and $Ic_3$ can be particularly reduced to a short period of time, when compared to a case where the diffraction grating or the specimen is repeatedly rotated and stopped for switching the direction of structured illumination.

Incidentally, in the method of rotating the diffraction grating or the specimen by using a rotation motor, a period of time required for stopping the diffraction grating or the specimen and a waiting time until when a vibration disappears after the stop of the diffraction grating or the specimen are long, and it is difficult to improve the speed of obtaining the series of nine pieces of image data $Ia_1$, $Ia_2$, $Ia_3$, $Ib_1$, $Ib_2$, $Ib_3$, $Ic_1$, $Ic_2$, and $Ic_3$.

Further, in the above-described steps S11, S12, S15, S16, S19, and S20, the frequency of AC voltage is adjusted in accordance with the temperature of the ultrasonic wave light modulator 3, so that it is possible to constantly keep the frequency to the appropriately frequency, to thereby constantly keep the high contrast of the structured illumination.

Therefore, the information regarding the structure of the fluorescent area of the specimen plane 10 is accurately reflected on the series of nine pieces of image data $Ia_1$, $Ia_2$, $Ia_3$, $Ib_1$, $Ib_2$, $Ib_3$, $Ic_1$, $Ic_2$, and $Ic_3$. Accordingly, the accuracy of obtaining the super-resolved image described above is highly maintained.

Further, in the present embodiment, the direction of structured illumination is set to three directions as illustrated in FIG. 4, but, there is provided only one piezoelectric actuator 22. Therefore, the configuration of the periphery of the ultrasonic wave light modulator 3 is simple.

Further, in the present embodiment, it is possible to form a plurality of diffraction gratings with different directions in a switchable manner, at the same position on the optical axis, so that even if the direction of structured illumination is switched, it is not necessary to perform readjustment of focal position and the like, resulting in that a high contrast and a reduction in the period of time of obtaining images, can be realized at the same time.

Moreover, according to the above-described steps S14, S18, and S22, the stroke corresponding to one step of the piezoelectric actuator 22 is switched in accordance with the direction of modulation of the ultrasonic wave light modulator 3, so that the amount of phase shift when the direction of structured illumination is the first direction Da, the amount of phase shift when the direction of structured illumination is the second direction Db, and the amount of phase shift when the direction of structured illumination is the third direction Dc, become equal.

Therefore, the image storing-calculating device 13 can set the calculation to be performed on the series of three pieces of image data $Ia_1$, $Ia_2$, and $Ia_3$, the calculation to be performed on the series of three pieces of image data $Ib_1$, $Ib_2$, and $Ib_3$, and the calculation to be performed on the series of three pieces of image data $Ic_1$, $Ic_2$, and $Ic_3$, to the common calculation.

As a result of this, according to the present embodiment, it is possible to prevent an enlargement of circuit scale of the image storing-calculating device 13 while simplifying the configuration of the periphery of the ultrasonic wave light modulator 3.

Supplement to First Embodiment

Note that the CPU of the present embodiment performs the frequency adjustment every time the series of three pieces of image data (the pieces of image data $Ia_1$, $Ia_2$, and $Ia_3$, the pieces of image data $Ib_1$, $Ib_2$, and $Ib_3$, or the pieces of image data $Ic_1$, $Ic_2$, and $Ic_3$) are obtained, but, it is also possible to perform the frequency adjustment for a predetermined period of time. Alternatively, it is also possible to measure a period of time of continuous energization with respect to the ultrasonic wave light modulator 3, and to perform the frequency adjustment every time the period of time of continuous energization reaches a predetermined period of time. However, in any of the above cases, it is desirable that the frequency is not changed in the middle of the obtainment of the series of three pieces of image data (the pieces of image data $Ia_1$, $Ia_2$, and $Ia_3$, the pieces of image data $Ib_1$, $Ib_2$, and $Ib_3$, or the pieces of image data $Ic_1$, $Ic_2$, and $Ic_3$).

Further, although the CPU of the present embodiment adjusts the frequency of AC voltage in accordance with the temperature of the ultrasonic wave light modulator 3, it is also possible to adjust an amplitude of AC voltage, instead of the frequency or in addition to the frequency. When the frequency of AC voltage is fixed, or when the frequency adjustment of AC voltage is insufficient, there is a possibility that the ultrasonic wave is deviated from the standing wave, and the contrast of structured illumination is lowered. However, in that case, if the amplitude of AC voltage is set to a rather high amplitude, an intensity of the structured illumination is increased, so that an increase in the calculation error described above can be suppressed to a certain degree.

Further, although the CPU of the present embodiment adjusts the frequency of AC voltage in accordance with the temperature of the ultrasonic wave light modulator 3, it is also possible to adjust a charge storing time of the imaging device 12, instead of the frequency or in addition to the frequency. This is because, when the frequency of AC voltage is fixed, or when the frequency adjustment of AC voltage is insufficient, there is a possibility that the ultrasonic wave is deviated from the standing wave, and the contrast of structured illumination is lowered. However, in that case, if the charge storing time of the imaging device 12 is set to a rather long time, a fluorescent image can be detected at a high exposure, so that an increase in the calculation error described above can be suppressed to a certain degree.

Further, the shape of the acousto-optical medium 15 of the ultrasonic wave light modulator 3 of the present embodiment is the regular hexagonal prism shape, but, the shape may also be another shape having a plurality of mutually opposing coupled side faces, such as, for example, a regular rectangular prism shape, and a regular octagonal prism shape.

Incidentally, when the shape of the acousto-optical medium 15 is the regular rectangular prism shape, the number of the transducers becomes two, and the direction of modulation of the ultrasonic wave light modulator 3 is set to two directions which are mutually different by 90°. Further, when the shape of the acousto-optical medium 15 is the regular octagonal prism shape, the number of the transducers becomes four, and the direction of modulation of the ultrasonic wave light modulator 3 is set to four directions which are mutually different by 45°.

However, the shape of the acousto-optical medium 15 is preferably the regular hexagonal prism shape, in terms of an efficiency of obtaining images. This is because, when the direction of modulation of the ultrasonic wave light modulator 3 is set to three directions which are mutually different by 60°, an amount of obtainable information is large, regardless of the small number of image data to be obtained (area of distribution of the plurality of pieces of demodulated image data in the wave number space is large).

Second Embodiment

Hereinafter, a second embodiment of the present invention will be described by using the drawings. The present embodiment is a modified example of the first embodiment. Here, only a point of difference between the present embodiment and the first embodiment will be described.

The point of difference is that a heat releasing function is added to the ultrasonic wave light modulator 3. Instead of that, a frequency of the frequency adjustment (or the amplitude adjustment or the charge storing time adjustment) in the present embodiment is reduced, compared to that in the first embodiment. Alternatively, the frequency adjustment (or the amplitude adjustment or the charge storing time adjustment) is omitted.

Figure 9:
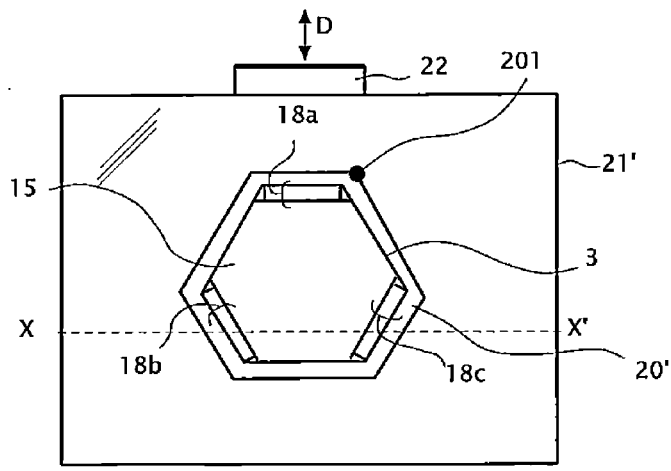
FIG. 9 is a diagram in which a periphery of an ultrasonic wave light modulator 3 in a second embodiment is seen from an optical axis direction.
Figure 10:
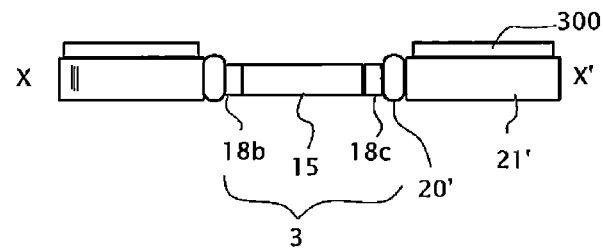
FIG. 10 is a sectional diagram obtained by cutting the ultrasonic wave light modulator 3 along a plane X-X' (plane being parallel to the optical axis and traversing transducers 18b and 18c) in FIG. 9.

FIG. 9 is a diagram in which a periphery of the ultrasonic wave light modulator 3 in the second embodiment is seen from an optical axis direction, and FIG. 10 is a sectional diagram obtained by cutting the ultrasonic wave light modulator 3 along a plane X-X' (plane being parallel to the optical axis and traversing transducers 18b and 18c) in FIG. 9.

A supporting frame 21' illustrated in FIG. 9 and FIG. 10 is made of a material with high heat conductivity such as aluminum, and a pad 20' interposed between the supporting frame 21' and the ultrasonic wave light modulator 3 is a pad-type heat releasing material that conducts heat of the ultrasonic wave light modulator 3 to the supporting frame 21'. The heat conductivity of the pad 20' is 1.7 W/mK, for example, and a thickness of the pad 20' is 0.5 mm, for example (as a pad with such a specification, there can be cited 5503S manufactured by 3M).

Further, as illustrated in FIG. 10, to a surface of the supporting frame 21', a Peltier element 300 is attached in a range where it does not block a light path of the ultrasonic wave light modulator 3. The Peltier element 300 operates to release heat of the supporting frame 21' to the atmosphere side.

Therefore, a mechanism formed of the Peltier element 300, the supporting frame 21', and the pad 20' operates to release heat generated in the ultrasonic wave light modulator 3 to a space separated from the ultrasonic wave light modulator 3.

Concretely, an amount of temperature rise in the ultrasonic wave light modulator 3 when energization is conducted for 100 seconds is 5.5° C. when this heat releasing function is not provided, but, when the heat releasing function is provided, the amount can be expected to be suppressed to about 0.6° C. Therefore, in the present embodiment, it is possible to regard that almost no change occurs in the appropriately frequency of AC voltage described above (refer to FIG. 7).

As a result of this, in the present embodiment, even if the frequency adjustment (or the amplitude adjustment or the charge storing time adjustment) is reduced, or if the frequency adjustment (or the amplitude adjustment or the charge storing time adjustment) is omitted, an accuracy of obtainment of super-resolved image can be kept to about the same as that of the first embodiment.

[Supplement to Structured Microscopy Apparatus and the Like Exemplifying the Present Invention]

Note that it is also possible that in the structured illumination microscopy apparatus exemplifying the present invention, the above-described ultrasonic wave light modulator includes a prismatic acousto-optical medium having a plurality of mutually opposing parallel coupled side faces and having a central axis arranged on the optical axis, and a plurality of ultrasonic wave transducers each generating an ultrasonic wave between the respective plurality of coupled side faces of the above-described acousto-optical medium.

Further, it is also possible that in the structured illumination microscopy apparatus exemplifying the present invention, the interference fringes projected onto the observational object are formed by using three or more light fluxes, out of a plurality of light fluxes generated by the diffraction grating.

Further, it is also possible that the structured illumination microscopy apparatus exemplifying the present invention further includes a signal generating unit generating a driving signal which changes with time in a sinusoidal manner, as a driving signal to be given to any one of the above-described plurality of ultrasonic wave transducers, and a switching unit switching an input destination of the driving signal generated by the above-described signal generating unit among the above-described plurality of ultrasonic wave transducers.

Further, it is also possible that in the structured illumination microscopy apparatus exemplifying the present invention, a frequency of the driving signal generated by the above-described signal generating unit is set to a frequency for making the ultrasonic wave generated in the above-described acousto-optical medium to be a standing wave.

Further, it is also possible that the structured illumination microscopy apparatus exemplifying the present invention further includes a temperature sensor detecting a temperature of the above-described acousto-optical medium, and an adjusting unit adjusting an exposure amount of the above-described image detector in accordance with the temperature detected by the above-described temperature sensor.

Further, it is also possible that the structured illumination microscopy apparatus exemplifying the present invention further includes a heat releasing unit releasing heat generated in the above-described acousto-optical medium.

Further, it is also possible that in the structured illumination microscopy apparatus exemplifying the present invention, the above-described phase shifting unit moves the above-described ultrasonic wave light modulator in steps in a direction which is not perpendicular to all of the above-described plurality of directions.

Further, it is also possible that in the structured illumination microscopy apparatus exemplifying the present invention, the above-described phase shifting unit changes the stroke corresponding to one step, in accordance with the direction of modulation of the above-described ultrasonic wave light modulator.

Third Embodiment

Hereinafter, a third embodiment of the present invention will be described by using the drawings. The present embodiment is a modified example of the first embodiment. Here, only a point of difference between the present embodiment and the first embodiment will be described.

Figure 11:
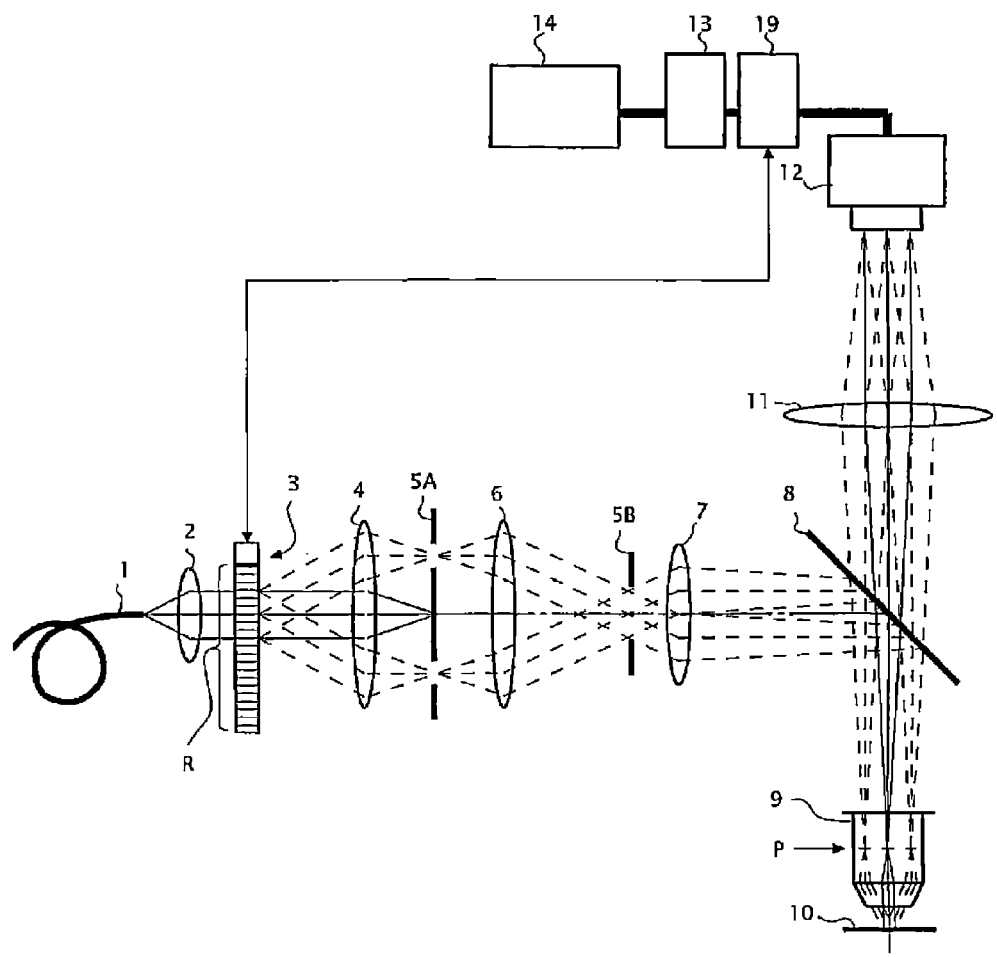
FIG. 11 is a configuration diagram of a structured illuminating microscopy system of a third embodiment.

FIG. 11 is a configuration diagram of a structured illuminating microscopy system of the present embodiment. As illustrated in FIG. 11, in the present embodiment, the piezoelectric actuator 22 is omitted, and the function of shifting the phase of the structured illumination is realized by the controlling device 19.

The controlling device 19 controls the ultrasonic standing wave generated in the ultrasonic wave propagation path R of the ultrasonic wave light modulator 3, to thereby change the amount of phase shift of the structured illumination, in steps, by $2\pi/3$ (details will be described later). Further, the controlling device 19 drives the imaging device 12 when the phases of structured illumination are in the respective states to obtain three types of image data $I_{-1}$, $I_0$, and $I_{+1}$, and sequentially sends those pieces of image data $I_{-1}$, $I_0$, and $I_{+1}$ to the image storing-calculating device 13.

The image storing-calculating device 13 performs separating calculation on the pieces of image data $I_{-1}$, $I_0$, and $I_{+1}$ which are taken therein, to thereby obtain image data I as a result of removing structure information of the structured illumination. Further, the image storing-calculating device 13 performs demodulating calculation on the image data I to obtain image data I' as a result of returning the spatial frequency of the structure information of the fluorescent area to the actual spatial frequency, and sends the image data I' to the image displaying device 14. Therefore, a resolved image that exceeds the resolution limit of the objective lens 9 (super-resolved image) is displayed on the image displaying device 14.

FIG. 12(A) is a schematic diagram illustrating a pattern of ultrasonic standing wave generated in the ultrasonic wave propagation path R, and FIG. 12(B) is a schematic diagram illustrating a pattern of structured illumination (arrangement of bright part and dark part) corresponding to the pattern (note that only a pattern of portion through which an effective light flux passes, out of the pattern of the ultrasonic wave propagation path R, is reflected on the actual structured illumination). Further, in FIG. 12(A), a wave number of the ultrasonic standing wave generated in the ultrasonic wave propagation path R is set to "2", which is smaller than the actual number, for easier understanding of the explanation.

As illustrated in FIG. 12(A), when the wave number of the ultrasonic standing wave (the wave number is counted as one when the phase is shifted by $2\pi$) is "2", a fringe number (number of bright part or dark part) of the structured illumination formed by the interference of ±first-order lights becomes "4", as illustrated in FIG. 12(B). Specifically, the fringe number of the structured illumination becomes twice the wave number of the ultrasonic standing wave corresponding to the fringe number.

Therefore, when the wave number of the ultrasonic standing wave is changed, by ½, in three ways such as 2, (2+½), and 3 (namely, when the wavelength of the ultrasonic standing wave is changed), as illustrated in FIG. 12(C), (D), and (E), the fringe number of the structured illumination corresponding to the wave number is changed, by one, in three ways such as 4, 5, and 6.

Figure 12:
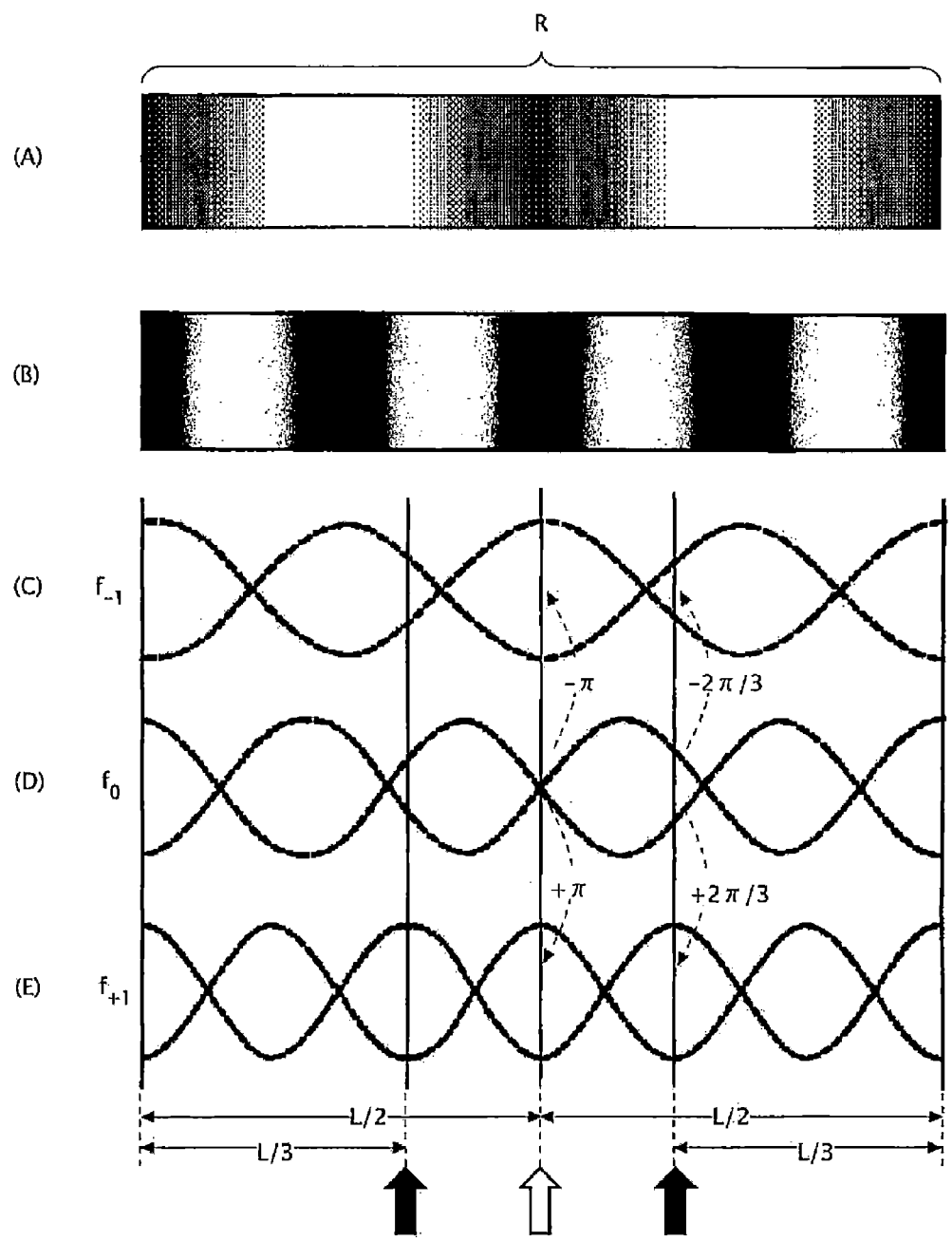
FIG. 12(A) is a schematic diagram illustrating a pattern of ultrasonic standing wave generated in an ultrasonic wave propagation path R of the ultrasonic wave light modulator 3.
FIG. 12(B) is a schematic diagram illustrating a pattern of structured illumination (arrangement of bright part and dark part) corresponding to the pattern.
FIG. 12(C) to (E) are diagrams explaining a change in a fringe number when a wave number is changed.

Here, if attention is focused only on a portion deviated by ½ from one end of the ultrasonic wave propagation path R, as indicated by a white arrow mark in FIG. 12, the phase of the structured illumination corresponding to the focused portion is shifted, by "$\pi$", in three ways.

Further, if attention is focused only on portions each deviated by ⅓ from one end of the ultrasonic wave propagation path R, as indicated by black arrow marks in FIG. 12, the phase of the structured illumination corresponding to each of the focused portions is shifted, by "$2\pi/3$", in three ways.

Accordingly, if an incident area of light with respect to the ultrasonic wave propagation path R is tentatively limited only to the position indicated by the white arrow mark, the phase of the structured illumination can be shifted by "$\pi$", only by changing the wave number of the ultrasonic standing wave by ½.

Further, if the incident area of light with respect to the ultrasonic wave propagation path R is tentatively limited only to the positions indicated by the black arrow marks, the phase of the structured illumination can be shifted by "$2\pi/3$", only by changing the wave number of the ultrasonic standing wave by ½.

Accordingly, in the present embodiment, in order to set the amount of phase shift per one step to $2\pi/3$, a distance D from a center of spot (effective diameter) S of light which is incident on the ultrasonic wave propagation path R to one end of the ultrasonic wave propagation path R, is set to one-third a length L in a propagation direction of the ultrasonic wave propagation path R (D=L/3).

Figure 13:
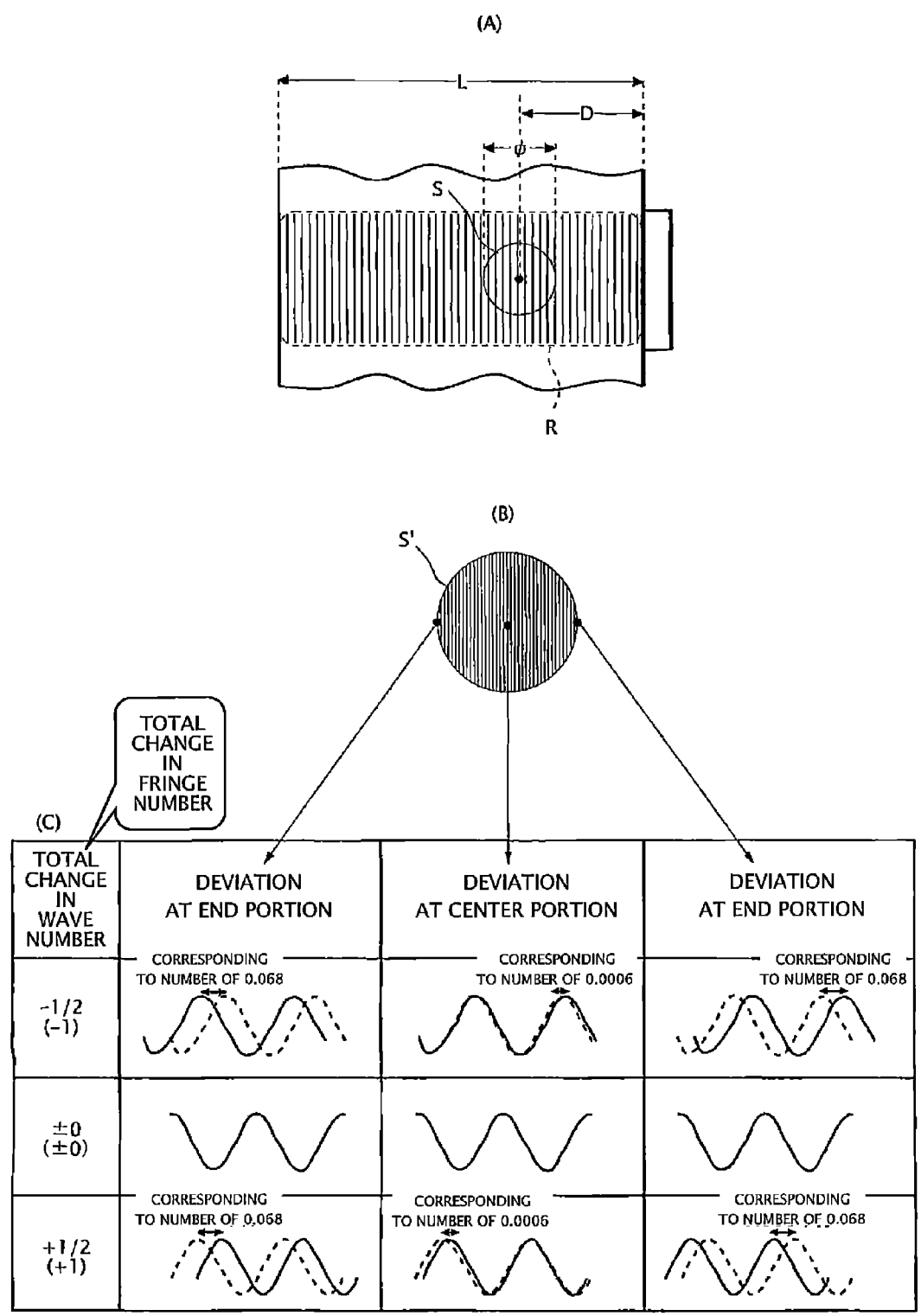
FIG. 13(A) is a diagram explaining a relation between a length L and a distance D.
FIG. 13(B) is a conceptual diagram of structured illumination S' corresponding to a spot S.
FIG. 13(C) is a diagram explaining a deviation of the fringe number of the structured illumination S'.

However, when the wave number of the ultrasonic standing wave generated in the ultrasonic wave propagation path R is changed by ½, the wave number of the ultrasonic standing wave generated in the inside of the spot S is also deviated a little, so that the fringe number of the structured illumination S' corresponding to the spot S is also deviated a little, as illustrated in FIG. 13(B) (note that the wave pattern and the fringe pattern illustrated in FIG. 13 are illustrated in a schematic manner, and thus the wave number and the fringe number do not always coincide with the actual numbers).

Therefore, in the present embodiment, the length L of the ultrasonic wave propagation path R is set to be large enough, compared to a diameter p of the spot S, so that the deviation of the fringe number of the structured illumination S' can be regarded as approximately zero.

Concretely, the length L of the ultrasonic wave propagation path R and the diameter $\phi$ of the spot S are set to satisfy a relation of $\phi/L<\delta$, with respect to an allowable amount $\delta$ of the deviation of the fringe number of the structured illumination S'. For example, if the deviation of the fringe number of the structured illumination S' is required to be suppressed to the number of 0.15 or less, the relational expression becomes $\phi/L \leq 0.15$.

Further, the diameter $\phi$ of the spot S does not always have to satisfy the relation of $\phi/L<\delta$ on the ultrasonic wave propagation path R of the ultrasonic wave light modulator 3, and when the ±first-order diffracted light outgone from the ultrasonic wave light modulator 3 is narrowed by the field stop 5B, for example, the length L of the ultrasonic wave propagation path R, a diameter $\phi'$ of illuminated area (observational area, field area) on the specimen plane 10, and an optical power m from the specimen plane 10 to the ultrasonic wave light modulator 3, are only required to be set to satisfy a relation of $\phi' \times m/L < \delta$, with respect to the allowable amount $\delta$ of the deviation of the fringe number of the structured illumination S'.

In the present embodiment, the diameter $\phi$ of the spot S is assumed to be 4 mm. In this case, if the length L of the ultrasonic wave propagation path R is set to 30 mm, the deviation of fringes at each of both ends of the structured illumination S' can be suppressed to one corresponding to about the number of 0.068, and the deviation of the fringe number in the entire area of the structured illumination S' can be suppressed to about the number of 0.68±0.68=0.13, as illustrated in FIG. 13(C). Note that in FIG. 13(C), a dotted line indicates an ideal pattern of the structured illumination S' (pattern when the deviation of the fringe number is zero), a solid line indicates an actual pattern of the structured illumination S', and a deviation of the both is illustrated in an exaggerated manner for easier understanding.

Figure 14:
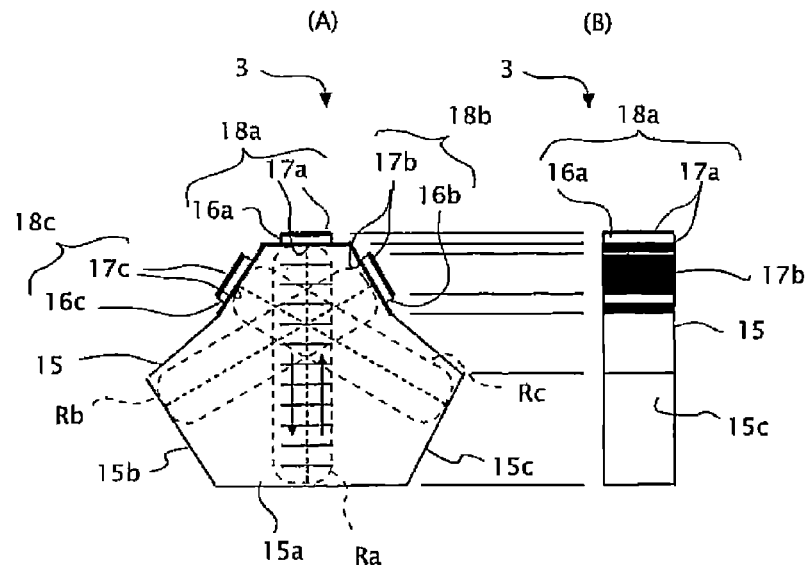
FIG. 14 is configuration diagrams of the ultrasonic wave light modulator 3.

FIG. 14 is configuration diagrams of the ultrasonic wave light modulator 3. FIG. 14(A) is a diagram in which the ultrasonic wave light modulator 3 is seen from the front (optical axis direction), and FIG. 14(B) is a diagram in which the ultrasonic wave light modulator 3 is seen from the side (direction perpendicular to the optical axis).

As illustrated in FIG. 14, the ultrasonic wave light modulator 3 includes an acousto-optical medium 15, and the acousto-optical medium 15 is set to have a prismatic shape having three pairs of mutually opposing parallel coupled side faces. Three transducers 18a, 18b, and 18c are individually provided on the three pairs of coupled side faces, on one side of each of the coupled side faces, and accordingly, three ultrasonic wave propagation paths are formed in one acousto-optical medium 15. Hereinafter, the ultrasonic wave propagation path formed between a formation face of the transducer 18a and a side face 15a opposing the formation face is set to an "ultrasonic wave propagation path Ra", the ultrasonic wave propagation path formed between a formation face of the transducer 18b and a side face 15b opposing the formation face is set to an "ultrasonic wave propagation path Rb", and the ultrasonic wave propagation path formed between a formation face of the transducer 18c and a side face 15c corresponding to the formation face is set to an "ultrasonic wave propagation path Rc".

Note that a material of the acousto-optical medium 15 is, for example, a quartz glass, a tellurite glass, a dense flint glass, a flint glass or the like, and the three pairs of coupled side faces and two bottom faces of the acousto-optical medium are respectively polished with sufficient precision.

Here, lengths L of the respective three ultrasonic wave propagation paths Ra, Rb, and Rc are common (L=30 mm), and the length L satisfies the aforementioned condition with respect to the diameter $\phi$ of the spot S described above.

Further, the three ultrasonic wave propagation paths Ra, Rb, and Rc intersect at angles different by 60° from each other, at a position separated by L/3 from one end of each of the paths. At a position of the intersection, a center of the above-described spot S is positioned.

The transducer 18a is an ultrasonic wave transducer having a piezoelectric body 16a and two electrodes 17a individually formed on upper and lower faces of the piezoelectric body 16a, and is joined to one side face of the acousto-optical medium 15 via the electrode 17a being one of the two electrodes 17a. When an AC voltage of high frequency is applied between the two electrodes 17a of the transducer 18a, the piezoelectric body 16a vibrates in a thickness direction, resulting in that a planar ultrasonic wave reciprocates in the ultrasonic wave propagation path Ra. When the frequency of AC voltage applied between the two electrodes 17a is set to a specific frequency (appropriately frequency), the ultrasonic wave becomes a standing wave, so that a distribution of sinusoidal shape is given to a refractive index in the ultrasonic wave propagation path, over a propagation direction of the ultrasonic wave. Accordingly, the ultrasonic wave propagation path Ra becomes a phase type diffraction grating having a phase grating perpendicular to the propagation direction of the ultrasonic wave. Hereinafter, the propagation direction in the ultrasonic wave propagation path Ra is referred to as a "first direction".

Further, the transducer 18b, which also has the same configuration as that of the transducer 18a, has a piezoelectric body 16b and two electrodes 17b individually formed on upper and lower faces of the piezoelectric body 16b, and is joined to one side face of the acousto-optical medium 15 via the electrode 17b being one of the two electrodes 17b.

Therefore, when an AC voltage of appropriately frequency is applied between the two electrodes 17b of the transducer 18b, a planar ultrasonic wave propagates in the ultrasonic wave propagation path Rb, so that the ultrasonic wave propagation path Rb becomes a phase type diffraction grating having a phase grating perpendicular to the propagation direction of the ultrasonic wave. Hereinafter, the propagation direction in the ultrasonic wave propagation path Rb is referred to as a "second direction". This second direction makes an angle of 60° with the first direction.

Further, the transducer 18c, which also has the same configuration as that of the transducer 18a, has a piezoelectric body 16c and two electrodes 17c individually formed on upper and lower faces of the piezoelectric body 16c, and is joined to one side face of the acousto-optical medium 15 via the electrode 17c being one of the two electrodes 17c.

Therefore, when an AC voltage of appropriately frequency is applied between the two electrodes 17c of the transducer 18c, a planar ultrasonic wave propagates in the ultrasonic wave propagation path Rc, so that the ultrasonic wave propagation path Rc becomes a phase type diffraction grating having a phase grating perpendicular to the propagation direction of the ultrasonic wave. Hereinafter, the propagation direction in the ultrasonic wave propagation path Rc is referred to as a "third direction". This third direction makes an angle of −60° with the first direction.

Figure 15:
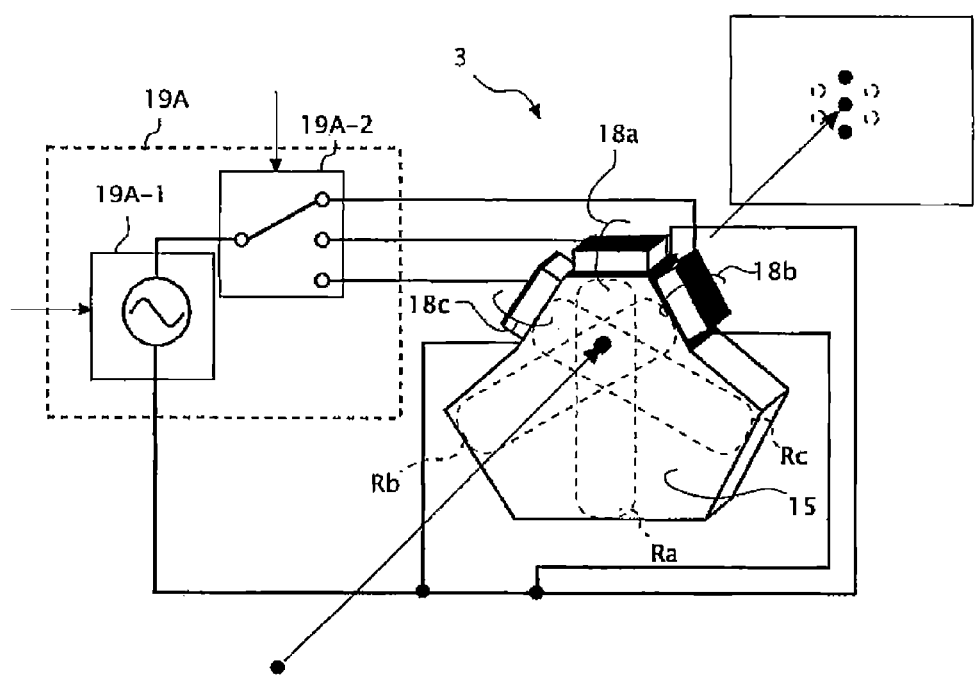
FIG. 15 is a diagram explaining a driving circuit 19A of the ultrasonic wave light modulator 3.

FIG. 15 is a diagram explaining a driving circuit 19A of the ultrasonic wave light modulator 3. This driving circuit 19A is a part of the controlling device 19 illustrated in FIG. 11.

As illustrated in FIG. 15, the driving circuit 19A includes a high-frequency AC power source 19A-1 and a selector switch 19A-2.

The high-frequency AC power source 19A-1 generates an AC voltage to be supplied to the ultrasonic wave light modulator 3. A frequency of the AC voltage is controlled to an appropriately frequency (any value within a range of several tens of MHz to 100 MHz, for example), by the CPU in the controlling device 19.

In the present embodiment, in order to change the amount of phase shift of the structured illumination S' described above in steps, in three ways of −2π/3, 0, and +2π/3, the CPU is set to be able to switch the frequency of the AC voltage among three ways of different appropriately frequencies $f_{-1}$, $f_0$, and $f_{+1}$.

For example, the appropriately frequency $f_0$ is an appropriately frequency (80 MHz) for generating ultrasonic standing waves whose number is 100 (the fringe number of the structured illumination corresponding thereto is 200) in the ultrasonic wave propagation paths Ra, Rb, and Rc each having the length L of 30 mm. According to the appropriately frequency $f_0$, the amount of phase shift of the structured illumination S' becomes zero.

In this case, the appropriately frequency $f_{-1}$ becomes an appropriately frequency (79.946 MHz) for generating ultrasonic standing waves whose number is (100−½) (the fringe number of the structured illumination corresponding thereto is 199) in the ultrasonic wave propagation paths Ra, Rb, and Rc each having the length L of 30 mm. According to the appropriately frequency $f_{-1}$, the amount of phase shift of the structured illumination S' becomes −2π/3.

Further, the appropriately frequency $f_{+1}$ becomes an appropriately frequency (80.054 MHz) for generating ultrasonic standing waves whose number is (100+½) (the fringe number of the structured illumination corresponding thereto is 201) in the ultrasonic wave propagation paths Ra, Rb, and Rc each having the length L of 30 mm. According to the appropriately frequency $f_{+1}$, the amount of phase shift of the structured illumination S' becomes +2π/3.

The selector switch 19A-2 is disposed between the high-frequency AC power source 19A-1 and the ultrasonic wave light modulator 3, and can switch a connection destination on the side of the ultrasonic wave light modulator 3, among the three transducers 18a, 18b, and 18c of the ultrasonic wave light modulator 3. The connection destination of the switch 19A-2 is appropriately switched by the CPU in the controlling device 19.

When the connection destination of the selector switch 19A-2 is on the side of the transducer 18a, the AC voltage is applied between the two electrodes of the transducer 18a, so that only the ultrasonic wave propagation path Ra among the three ultrasonic wave propagation paths Ra, Rb, and Rc, becomes effective.

Further, when the connection destination of the selector switch 19A-2 is on the side of the transducer 18b, the AC voltage is applied between the two electrodes of the transducer 18b, so that only the ultrasonic wave propagation path Rb among the three ultrasonic wave propagation paths Ra, Rb, and Rc, becomes effective.

Further, when the connection destination of the selector switch 19A-2 is on the side of the transducer 18c, the AC voltage is applied between the two electrodes of the transducer 18c, so that only the ultrasonic wave propagation path Rc among the three ultrasonic wave propagation paths Ra, Rb, and Rc, becomes effective.

As above, when the effective ultrasonic wave propagation path is switched among the three ultrasonic wave propagation paths Ra, Rb, and Rc, the direction of structured illumination S' can be switched among a direction corresponding to the first direction, a direction corresponding to the second direction, and a direction corresponding to the third direction.

Figure 16:
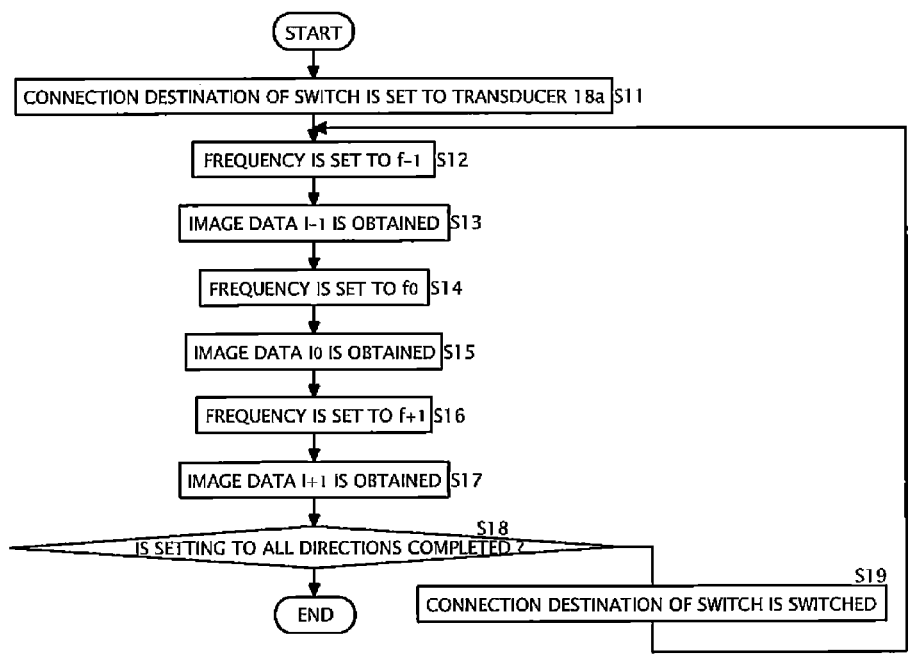
FIG. 16 is an operational flow chart of a CPU in the third embodiment.

FIG. 16 is an operational flow chart of the CPU in the third embodiment. Hereinafter, respective steps will be described in order.

Step S11: The CPU sets the connection destination of the selector switch 19A-2 to a first transducer (transducer 18a) side, to thereby set the direction of structured illumination S' to the direction corresponding to the first direction.

Step S12: The CPU sets the frequency of AC voltage generated by the high-frequency AC power source 19A-1 to the appropriately frequency $f_{-1}$, to thereby set the amount of phase shift of the structured illumination S' to $-2\pi/3$.

Step S13: The CPU drives the imaging device 12 under this state to obtain image data $I_{-1}$.

Step S14: The CPU sets the frequency of AC voltage generated by the high-frequency AC power source 19A-1 to the appropriately frequency $f_0$, to thereby set the amount of phase shift of the structured illumination S' to zero.

Step S15: The CPU drives the imaging device 12 under this state to obtain image data $I_0$.

Step S16: The CPU sets the frequency of AC voltage generated by the high-frequency AC power source 19A-1 to the appropriately frequency $f_{+1}$, to thereby set the amount of phase shift of the structured illumination S' to $+2\pi/3$.

Step S17: The CPU drives the imaging device 12 under this state to obtain image data $I_{+1}$.

Step S18: The CPU judges whether or not the setting of direction of the structured illumination S' to all of the above-described three directions is completed, in which when the setting is not completed, the process proceeds to step S19, and when the setting is completed, the flow is terminated.

Step S19: The CPU switches the direction of structured illumination S' by switching the connection destination of the selector switch 19A-2, and then the process proceeds to step S12.

According to the above-described flow, pieces of image data $Ia_{-1}$, $Ia_0$, and $Ia_{+1}$, regarding the first direction, pieces of image data $Ib_{-1}$, $Ib_0$, and $Ib_{+1}$, regarding the second direction, and pieces of image data $Ic_{-1}$, $Ic_0$, and $Ic_{+1}$ regarding the third direction are obtained. These pieces of image data are taken into the image storing-calculating device 13.

The image storing-calculating device 13 performs separating calculation with the use of linear calculation on the series of three pieces of image data $Ia_{-1}$, $Ia_0$, and $Ia_{+1}$, to obtain image data Ia including no structure information of the structured illumination S', and performs demodulating calculation with the use of multiplication with a demodulation coefficient on the image data Ia, to obtain demodulated image data Ia' of super-resolved image along the first direction.

Further, the image storing-calculating device 13 performs separating calculation with the use of linear calculation on the series of three pieces of image data $Ib_{-1}$, $Ib_0$, and $Ib_{+1}$, to obtain image data Ib including no structure information of the structured illumination S', and performs demodulating calculation with the use of multiplication with a demodulation coefficient on the image data Ib, to obtain demodulated image data Ib' of super-resolved image along the second direction.

Further, the image storing-calculating device 13 performs separating calculation with the use of linear calculation on the series of three pieces of image data $Ic_{-1}$, $Ic_0$, and $Ic_{+1}$, to obtain image data Ic including no structure information of the structured illumination S', and performs demodulating calculation with the use of multiplication with a demodulation coefficient on the image data Ic, to obtain demodulated image data Ic' of super-resolved image along the third direction.

Further, the image storing-calculating device 13 combines the three pieces of demodulated image data Ia', Ib', and Ic' on a wave number space, then returns the resultant to the real space again to obtain image data I of super-resolved image along the first direction, the second direction, and the third direction, and sends the image data I to the image displaying device 14. Therefore, the super-resolved image representing the structure of the fluorescent area of the specimen plane 10 in detail, is displayed on the image displaying device 14.

As described above, in the present embodiment, the length L of the ultrasonic wave propagation path R, the diameter φ of the spot S, and the distance D from one end of the ultrasonic wave propagation path R to the center of the spot S, are set to satisfy the optimum relation described above, so that the phase of the structured illumination S' can be switched only by electrically switching the frequency of AC voltage given to the ultrasonic wave light modulator 3. A period of time required for the switching is short, and can be reduced to 10 ms or less even including a time constant of the circuit system including the power source.

Therefore, a period of time required for obtaining the series of image data can be particularly reduced to a short period of time, when compared to a case where the optical element or the specimen is mechanically moved for switching the phase of the structured illumination S'.

Further, in the present embodiment, there is no need to mechanically move the optical element or the specimen for switching the phase of the structured illumination S', so that the configuration of the periphery of the optical system can be simplified.

Further, in the present embodiment, three ultrasonic wave propagation paths Ra, Rb, and Rc with different angles are formed in one acousto-optical medium 15, so that the direction of structured illumination S' can be switched only by electrically changing the connection state of the selector switch 19A-2. A period of time required for the switching is short, and can be reduced to 10 ms or less even including a time constant of the circuit system including the power source.

Therefore, a period of time required for obtaining the series of image data can be particularly reduced to a short period of time, when compared to a case where the optical element or the specimen is mechanically rotated for switching the direction of structured illumination S'.

Figure 17:
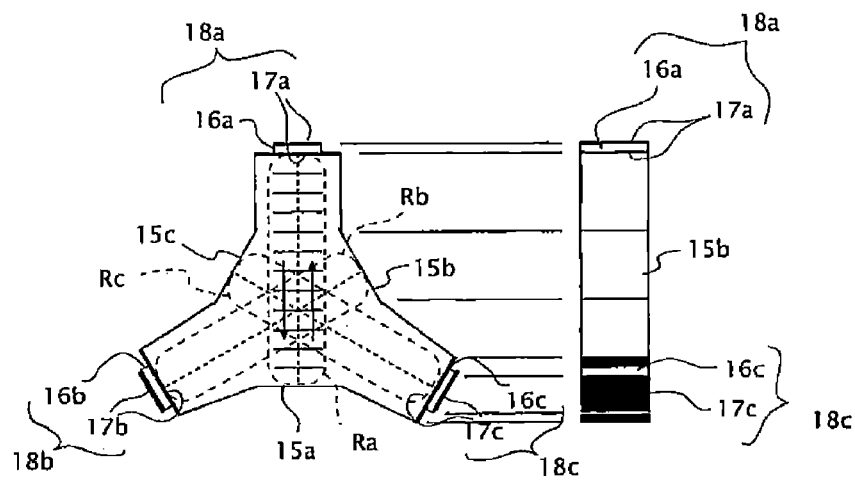
FIG. 17 is a modified example of the ultrasonic wave light modulator 3.

Note that in the acousto-optical medium 15 of the present embodiment, the three ultrasonic wave propagation paths Ra, Rb, and Rc are disposed in an asymmetric manner relative to the center of the spot S (refer to FIG. 14), but, they may also be disposed in a symmetric manner as illustrated in FIG. 17, for example. Incidentally, an advantage of the example illustrated in FIG. 14 is that projections and depressions of the outer shape of the acousto-optical medium 15 are small, and an advantage of the example illustrated in FIG. 17 is that environments of the three ultrasonic wave propagation paths Ra, Rb, and Rc completely coincide with one another.

Further, in the above-described explanation, the lengths of the ultrasonic wave propagation paths Ra, Rb, and Rc are set to common, and change patterns of frequency of the AC voltage given to the transducers 18a, 18b, and 18c are set to common, but, the present invention is not limited to this.

Further, in the above-described explanation, the change pattern of frequency of the AC voltage given to each of the transducers 18a, 18b, and 18c is set to a pattern in which the wave number of the ultrasonic standing wave is changed by ½, but, the present invention is not limited to this.

Further, in the above-described explanation, in order to set the phase shift amount of the structured illumination S' in each of the first direction, the second direction and the third direction to $2\pi/3$, the distance D from the center of the spot (effective diameter) S to the end portion of each of the ultrasonic wave propagation paths Ra, Rb, and Rc is set to one-third the length L in the propagation direction of the ultrasonic wave propagation path R (D=L/3), but, the present invention is not limited to this.

Concretely, the respective ultrasonic wave propagation paths Ra, Rb, and Rc are only required to individually satisfy the following conditions.

First, the change pattern of frequency of the AC voltage given to the transducer is only required to be a pattern in which the wave number of the ultrasonic standing wave is changed by M/2 (where |M| is an integer of 1 or more).

Further, in order to set the phase shift amount of the structured illumination S' to an arbitrary value $\Delta_\psi$, the distance D from either end portion of the ultrasonic wave propagation path to the center of partial area (spot S, for example), and the total length L of the ultrasonic wave propagation path are only required to satisfy a relation of D:L=$\Delta_\psi$/M:$2\pi$.

Note that a passage area of exit flux of light (spot) on the ultrasonic wave propagation path R of the ultrasonic wave light modulator 3 does not always have to be limited to the partial area separated from both ends of the ultrasonic wave propagation path R, for forming the interference fringes on the specimen plane 10, and when, for example, the light flux passed through the ultrasonic wave propagation path R is narrowed by the field stop 5B, the partial area of the ultrasonic wave propagation path R probably passed by the exit flux of light that contributes to the interference fringes (structured illumination S') formed on the illuminated area (observational area, field area) on the specimen plane 10, is only required to satisfy the relation of D:L=$\Delta_\psi$/M:$2\pi$.

Incidentally, if it is set that M=1, the number of ultrasonic standing wave is changed only by ½, so that the deviation occurred, due to the change, in the fringe number of the structured illustration S' can be minimized.

Further, if it is set that $\Delta_\psi$=$2\pi/k$ (where |k| is an integer of 2 or more), it is possible to securely obtain the pieces of image data (the plurality of pieces of image data) required for the aforementioned separating calculation (note that in the above-described explanation, the number of pieces of required image data is three, because the phase shift amount $\Delta_\psi$ is set to $2\pi/3$, but, if the phase shift amount $\Delta_\psi$ takes another value, the number of pieces of required image data is sometimes other than three).

Note that in the present embodiment, the modified example of the first embodiment is explained, but, it goes without saying that the second embodiment may also be modified in a similar manner.

Fourth Embodiment

Hereinafter, a fourth embodiment of the present invention will be described using the drawings. The present embodiment is an embodiment of a profile measuring apparatus.

Figure 18:
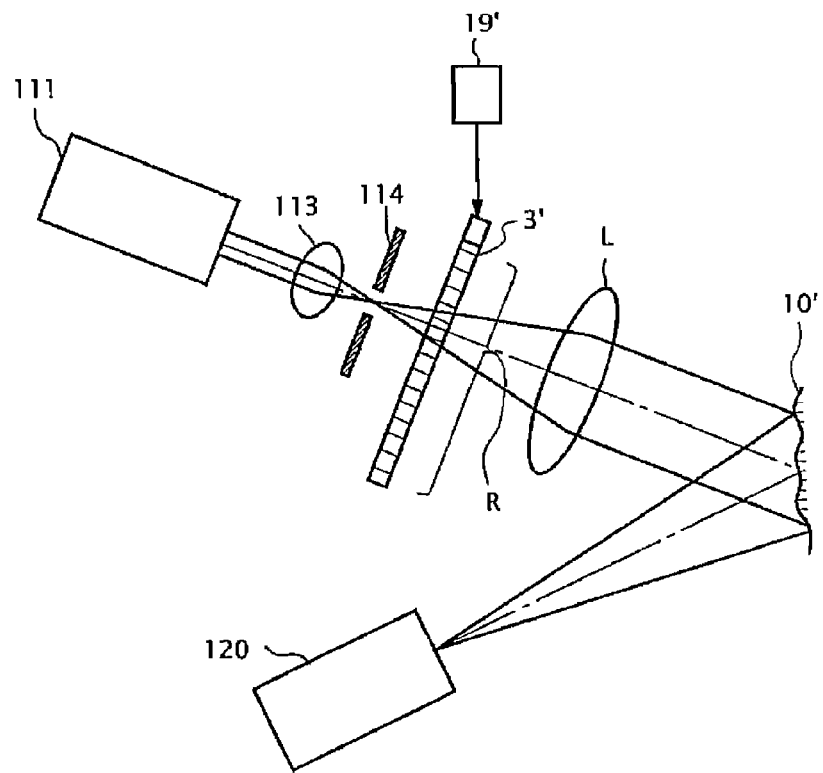
FIG. 18 is a configuration diagram of a profile measuring apparatus of a fourth embodiment.

FIG. 18 is a configuration diagram of a profile measuring apparatus (pattern projection type profile measuring apparatus) of the present embodiment. As illustrated in FIG. 18, in the profile measuring apparatus, a coherent light source (laser light source) 111, a controlling device 19', a lens 113, a pinhole element 114, an ultrasonic wave light modulator 3', a collimator lens L, and an imaging part 120, are disposed. A reference numeral 10' in FIG. 18 denotes a surface (measuring object plane) 10' of measuring object placed on a not-illustrated stage. Out of the above, the coherent light source 111, the lens 113, the pinhole element 114, the ultrasonic wave light modulator 3', the collimator lens L, and the controlling device 19' form a projecting part projecting a fringe pattern onto the measuring object plane 10', and the projecting part is disposed so that an optical axis becomes oblique to a reference plane of the not-illustrated stage.

Figure 19:
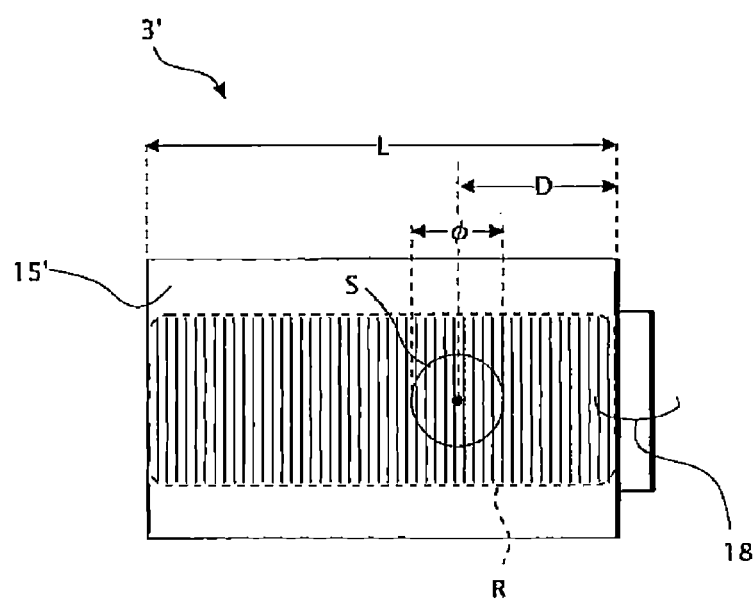
FIG. 19 is a configuration diagram of an ultrasonic wave light modulator 3'.

To the ultrasonic wave light modulator 3', an ultrasonic wave light modulator similar to the ultrasonic wave light modulator explained in the third embodiment is applied. Respective parameters such as L, $\phi$, D, M, $\Delta_\psi$, and k described above are set to satisfy the optimum relation similar to that of the third embodiment. Note that the ultrasonic wave light modulator 3' of the present embodiment is not required to switch the branch direction of light, so that there is no problem if an acousto-optical medium 15' of the ultrasonic wave light modulator 3' is set to have a rectangular prism shape, and the number of ultrasonic wave propagation path R formed in the inside of the medium is set to one, as illustrated in FIG. 19, for example.

The ultrasonic wave light modulator 3' operates as a phase type diffraction grating by generating an ultrasonic standing wave in the ultrasonic wave propagation path R, similar to the third embodiment. The diffracted light branched by the ultrasonic wave light modulator 3' forms interference fringes on the measuring object plane 10'.

The controlling device 19' can switch a frequency of AC voltage given to the ultrasonic wave light modulator 3' in a similar pattern to that explained in the third embodiment. Accordingly, a phase of fringes projected onto the measuring object plane 10' is switched in a similar manner to the phase of the structured illumination S' in the third embodiment.

The imaging part 120 is disposed so that an optical axis thereof becomes perpendicular to the reference plane of the not-illustrated stage, and captures an image of the measuring object plane 10' onto which the fringes are projected. This imaging part 120 has an image-forming optical system forming an image with reflected light from the measuring object plane 10', and an imaging element capturing an image of the measuring object plane 10'.

The imaging part 120 captures images of the measuring object plane 10' when the phases of fringes are in the respective states, and sends a plurality of pieces of image data obtained through the capturing of images (three pieces of image data, when the phase shift amount is $2\pi/3$) to a not-illustrated calculating device. The calculating device applies the plurality of pieces of image data to a predetermined arithmetic expression (expression of 3-bucket method, when the phase shift amount is $2\pi/3$), to thereby calculate a height of each position of the measuring object plane 10'.

As above, in the profile measuring apparatus of the present embodiment, the phase of fringes projected onto the measuring objet plane 10' is switched, and in the switching, it is only required to electrically switch the frequency of AC voltage.

Therefore, a period of time required for obtaining the series of image data (three pieces of image data, when the phase shift amount is $2\pi/3$) can be particularly reduced to a short period of time, when compared to a case where the optical element or the measuring object is mechanically moved for switching the phase of fringes. Note that in the present embodiment, explanation is made by using the example in which the interference fringes formed of ±first-order diffracted lights (structured illumination using two light fluxes) are formed on the specimen plane 10 (in X-Y plane, when the optical axis is set to a Z direction), but, the present invention can of course be applied to a case where interference fringes formed of 0th-order diffracted light and ±first-order diffracted lights (structured illumination using three light fluxes with which interference fringes are formed also in the optical axis direction) are formed on the specimen.

Further, in the present embodiment, it is explained that the frequency of AC voltage given to the transducers 18a, 18b, and 18c of the ultrasonic wave light modulator 3 is changed in the predetermined pattern, as one method of changing the wave number of the ultrasonic standing wave, namely, the wavelength of the ultrasonic standing wave generated in the ultrasonic wave propagation paths Ra, Rb, and Rc, in the predetermined pattern, for shifting the phase of interference fringes formed of ±first-order diffracted lights, but, it goes without saying that the present invention is not limited to this method.

Specifically, although the present embodiment explains the example of application of the ultrasonic wave light modulator of the third embodiment (profile measuring apparatus), it goes without saying that the ultrasonic wave light modulator of the first embodiment or the second embodiment can also be applied in a similar manner.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A structured illumination apparatus, comprising:
   a single light modulator being disposed in an exit flux of light from a light source, and in which a sonic wave propagation path is arranged in a direction traversing the exit flux of light;
   a sonic standing wave driver generating a sonic standing wave in the sonic wave propagation path by giving a driving signal for vibrating a medium of the sonic wave propagation path to the single light modulator; and
   an illuminating optical system comprising a lens, the illuminating optical system making mutually different diffracted components of the exit flux of light passed through the single light modulator that generates the sonic standing wave to be interfered with each other, and forming interference fringes of the diffracted components on an observational object.

2. The structured illumination apparatus according to claim 1, wherein
   the sonic standing wave driver generates the sonic standing wave by setting a frequency of the driving signal given to the single light modulator to a predetermined frequency.

3. The structured illumination apparatus according to claim 2, further comprising:
   a temperature sensor detecting a temperature of the medium of the sonic wave propagation path; and
   an adjuster adjusting at least one of the frequency and an amplitude of the driving signal in accordance with the temperature of the medium of the sonic wave propagation path.

4. The structured illumination apparatus according to claim 3, wherein
   the adjuster adjusts the frequency of the driving signal in accordance with the temperature being detected by the temperature sensor.

5. The structured illumination apparatus according to claim 3, wherein
   the adjuster adjusts the amplitude of the driving signal in accordance with the temperature being detected by the temperature sensor.

6. The structured illumination apparatus according to claim 1, further comprising
   a heat releaser releasing heat being generated in the medium of the sonic wave propagation path.

7. The structured illumination apparatus according to claim 1, further comprising
   a phase shifter shifting a phase of the interference fringes.

8. The structured illumination apparatus according to claim 7, wherein
   the phase shifter comprising a driver moving the single light modulator in a predetermined direction.

9. The structured illumination apparatus according to claim 8, wherein
   the driver changes a movement amount in accordance with a direction of the sonic standing wave.

10. The structured illumination apparatus according to claim 7, wherein:
    the exit flux of light contributing to the interference fringes is the exit flux of light passed through a predetermined partial area separated from both ends of the sonic wave propagation path; and
    the phase shifter is the sonic standing wave driver which shifts the phase of the interference fringes by changing a wavelength of the sonic standing wave in a predetermined pattern.

11. The structured illumination apparatus according to claim 10, wherein
    the sonic standing wave driver changes the wavelength of the sonic standing wave by changing the frequency of the driving signal given to the single light modulator in a predetermined pattern.

12. The structured illumination apparatus according to claim 11, wherein:
    the sonic standing wave driver changes the frequency in a pattern in which a total wave number of the sonic standing wave is changed by M/2, where |M| is an integer of 1 or more; and
    when a phase shift amount of the interference fringes is set to $\Delta\psi$, a distance D from either end portion of the sonic wave propagation path to the partial area and a total length L of the sonic wave propagation path are set to satisfy a relation of $D:L=\Delta\psi/M:2\pi$.

13. The structured illumination apparatus according to claim 12, wherein
    M equals to 1.

14. The structured illumination apparatus according to claim 12, wherein
    $\Delta\psi$ equals to $2\pi/k$, where |k| is an integer of 2 or more.

15. The structured illumination apparatus according to claim 10, wherein the single light modulator has a plurality of the sonic wave propagation path which intersects at the partial area.

16. The structured illumination apparatus according to claim 15, wherein
the single light modulator comprises a prismatic acousto-optical medium having a plurality of mutually opposing parallel coupled side faces, and a plurality of ultrasonic wave transducers each generating the sonic standing wave in the sonic wave propagation path formed between each of the plurality of coupled side faces.

17. The structured illumination apparatus according to claim 15, wherein
a disposition relation of the plurality of the sonic wave propagation path is set to make a direction of the interference fringes to be switchable among mutually different plurality of directions in a plane orthogonal to an optical axis of the illuminating optical system.

18. The structured illumination apparatus according to claim 16, further comprising:
a signal generator generating the driving signal given to any one of the plurality of ultrasonic wave transducers; and
a switch switching an input destination of the driving signal being generated by the signal generator among the plurality of ultrasonic wave transducers.

19. A structured illumination microscopy apparatus, comprising:
the structured illumination apparatus according to claim 1; and
an image-forming optical system comprising another lens, the image-forming optical system forming, on a detector, an image with observational light flux from the observational object illuminated by the structured illumination apparatus.

20. The structured illumination microscopy apparatus according to claim 19, further comprising:
a temperature sensor detecting a temperature of the medium of the sonic wave propagation path; and
an adjuster adjusting an exposure amount of the detector in accordance with the temperature of the medium of the sonic wave propagation path.

21. The structured illumination microscopy apparatus according to claim 19, wherein
the observational light flux is a fluorescent light flux.

22. The structured illumination microscopy apparatus according to claim 19, further comprising
a calculator calculating a super-resolved image of the observational object based on a plurality of images sequentially obtained by the detector while changing a wavelength of the sonic standing wave.

23. A profile measuring apparatus, comprising:
the structured illumination apparatus according to claim 1;
an image detector detecting an image of the observational object illuminated by the structured illumination apparatus; and
a calculator calculating a profile of the observational object based on a plurality of images sequentially obtained by the image detector while changing a wavelength of the sonic standing wave.

24. A structured illumination microscopy apparatus, comprising:
a light modulator being disposed in an exit flux of light from a light source, and in which a sonic wave propagation path is arranged in a direction traversing the exit flux of light;
a driver generating a sonic standing wave in the sonic wave propagation path by giving a driving signal for vibrating a medium of the sonic wave propagation path to the light modulator;
an illuminating optical system comprising a lens, the illuminating optical system making mutually different diffracted components of the exit flux of light passed through the sonic wave propagation path to be interfered with each other, and forming interference fringes of the diffracted components on an observational object;
an image-forming optical system comprising another lens forming, on a detector, an image with observational light flux from the observational object illuminated by the structured illumination apparatus;
a temperature sensor detecting a temperature of the medium of the sonic wave propagation path; and
an adjuster adjusting an exposure amount of the detector in accordance with the temperature of the medium of the sonic wave propagation path.

* * * * *